(12) United States Patent
Hauck et al.

(10) Patent No.: US 8,372,886 B2
(45) Date of Patent: Feb. 12, 2013

(54) TREATMENT OF RENAL DISORDERS, DIABETIC NEPHROPATHY AND DYSLIPIDEMIAS

(75) Inventors: Wendy Hauck, Baie D'Urfe (CA); Pavel Hamet, Ville Mont-Royal (CA)

(73) Assignee: Kiacta Sarl, St. Legier (CH)

( * ) Notice: Subject to any disclaimer, the term of this patent is extended or adjusted under 35 U.S.C. 154(b) by 0 days.

(21) Appl. No.: 11/643,946

(22) Filed: Dec. 22, 2006

(65) Prior Publication Data

US 2007/0238788 A1    Oct. 11, 2007

Related U.S. Application Data

(60) Provisional application No. 60/753,072, filed on Dec. 22, 2005.

(51) Int. Cl.
| | |
|---|---|
| A01N 37/00 | (2006.01) |
| A01N 43/36 | (2006.01) |
| A01N 43/42 | (2006.01) |
| A61K 38/00 | (2006.01) |

(52) U.S. Cl. ......... 514/578; 514/423; 514/311; 514/1.1; 514/292

(58) Field of Classification Search .................... 514/553
See application file for complete search history.

(56) References Cited

U.S. PATENT DOCUMENTS

| | | | |
|---|---|---|---|
| 2,531,468 A | 11/1950 | Reynolds et al. | |
| 3,174,901 A | 3/1965 | Sterne | |
| 3,218,352 A | 11/1965 | Freitelder et al. | |
| 3,236,881 A | 2/1966 | Distler et al. | |
| 3,658,966 A | 4/1972 | Tsunoo et al. | |
| 3,920,833 A | 11/1975 | Cook et al. | |
| 4,255,448 A | 3/1981 | Fariello | |
| 4,355,043 A | 10/1982 | Durlach | |
| 4,386,081 A | 5/1983 | Helgstrand et al. | |
| 4,448,779 A | 5/1984 | Blachard et al. | |
| 4,528,184 A | 7/1985 | Kurono et al. | |
| 4,657,704 A | 4/1987 | Yamamoto et al. | |
| 4,713,376 A | 12/1987 | Kuzuya et al. | |
| 4,737,353 A | 4/1988 | Flanigen et al. | |
| 4,847,082 A | 7/1989 | Sabin | |
| 4,883,666 A | 11/1989 | Sabel et al. | |
| 4,956,347 A | 9/1990 | Ban et al. | |
| 4,990,606 A | 2/1991 | Gennari | |
| 5,064,923 A | 11/1991 | Kashihara et al. | |
| 5,091,432 A | 2/1992 | Glasky | |
| 5,164,295 A | 11/1992 | Kisilevsky et al. | |
| 5,192,753 A | 3/1993 | McGeer et al. | |
| 5,242,932 A | 9/1993 | Gandy et al. | |
| 5,276,059 A | 1/1994 | Caughey et al. | |
| 5,318,958 A | 6/1994 | Kisilevsky | |
| 5,342,977 A | 8/1994 | Baschang et al. | |
| 5,385,915 A | 1/1995 | Buxbaum et al. | |
| 5,389,623 A | 2/1995 | Bodor | |
| 5,430,052 A | 7/1995 | Higashiura et al. | |
| 5,455,044 A | 10/1995 | Kim et al. | |
| 5,463,092 A | 10/1995 | Hostetler et al. | |
| 5,496,807 A | 3/1996 | Marchi et al. | |
| 5,622,981 A | 4/1997 | Eveleth et al. | |
| 5,643,562 A * | 7/1997 | Kisilevsky et al. | ........ 424/78.31 |
| 5,668,117 A | 9/1997 | Shapiro | |
| 5,723,496 A | 3/1998 | Nakada | |
| 5,728,375 A | 3/1998 | Kisilevsky et al. | |
| 5,780,510 A | 7/1998 | Carney | |
| 5,837,672 A | 11/1998 | Schenk et al. | |
| 5,840,294 A | 11/1998 | Kisilevsky et al. | |
| 5,858,326 A | 1/1999 | Kisilevsky et al. | |
| 5,869,469 A | 2/1999 | Szarek et al. | |
| 5,972,328 A | 10/1999 | Kisilevsky et al. | |
| 5,989,592 A | 11/1999 | Collin | |
| 6,015,835 A | 1/2000 | Miyamoto et al. | |
| 6,294,583 B1 | 9/2001 | Fogel | |
| 6,306,909 B1 | 10/2001 | Weaver et al. | |
| 6,310,073 B1 | 10/2001 | Kisilevsky et al. | |
| 6,316,501 B1 | 11/2001 | Miyamoto et al. | |
| 6,329,356 B1 | 12/2001 | Szarek et al. | |
| 6,376,557 B1 | 4/2002 | Zaveri | |
| 6,440,952 B2 | 8/2002 | Szarek et al. | |
| 6,562,836 B1 | 5/2003 | Szarek et al. | |
| 6,670,399 B2 | 12/2003 | Green et al. | |
| 6,689,816 B2 | 2/2004 | Fogel | |
| 6,746,678 B1 | 6/2004 | Shapiro | |

(Continued)

FOREIGN PATENT DOCUMENTS

| | | |
|---|---|---|
| DE | 4004978 A1 | 8/1991 |
| DE | 4004978 W | 8/1991 |

(Continued)

OTHER PUBLICATIONS

Aaltonen et al. (Changes in the Expression of Nephrin Gene and Protein in Experimental Diabetic Nephropathy, Lab Invest 2001, 81:1185-1190.*
Ravindran et al. (Case Report: response in proteinuria due to AA amyloidosis but not Felty's syndrome in a patient with rheumatoid arthritis treated with TNF-alpha blockade, Rheumatology, 2004; 43:669-672.*
Rosario R. and Prabhakar S., Lipids and Diabetic Nephropathy. Current Diabetes Reports (2006) vol. 6, pp. 455-462.
Wittmann I. et al., Prevention and treatment of diabetic nephropathy. Diabetes Research and Clinical Practice 68S1 (2005), pp. S36-D42.
Russell T., Diabetic Nephropathy in Patients with Type 1 Diabetes Mellitus. Nephrology Nursing Journal (2006), vol. 33, No. 1, pp. 15-30.

(Continued)

*Primary Examiner* — Sreeni Padmanabhan
*Assistant Examiner* — Timothy E Betton
(74) *Attorney, Agent, or Firm* — Foley & Lardner LLP

(57) ABSTRACT

Disclosed herein are methods, compounds and compositions for preventing or treating a renal disorder or chronic kidney diseases, including nephropathies such as diabetic nephropathy. The invention generally includes administering to a subject 1,3-propanedisulfonic acid or a pharmaceutically acceptable salt thereof, e.g., 1,3-propanedisulfonic acid sodium salt. The invention also relates to methods, compounds and compositions for the prevention and/or treatment of for preventing or treating a renal disorder complication. The invention further relates to methods, compounds and compositions for the prevention and/or treatment of dyslipidemia, and more particularly for reducing levels of harmful serum lipid levels, especially cholesterol and triglycerides in diabetic patients.

25 Claims, 4 Drawing Sheets

U.S. PATENT DOCUMENTS

| | | | |
|---|---|---|---|
| 6,930,112 B2 | 8/2005 | Weaver et al. | |
| 7,030,146 B2 | 4/2006 | Baynes et al. | |
| 7,244,764 B2 | 7/2007 | Kong et al. | |
| 7,253,306 B2 | 8/2007 | Kong et al. | |
| 7,259,152 B2 | 8/2007 | Palazzini et al. | |
| 7,262,223 B2 | 8/2007 | Kong et al. | |
| 2001/0048941 A1 | 12/2001 | Kisilevsky et al. | |
| 2002/0022657 A1 | 2/2002 | Gervais et al. | |
| 2002/0115717 A1 | 8/2002 | Gervais et al. | |
| 2002/0193395 A1 | 12/2002 | Kisilevsky et al. | |
| 2003/0027796 A1 | 2/2003 | Szarek et al. | |
| 2003/0077833 A1 | 4/2003 | Campbell et al. | |
| 2003/0108595 A1 | 6/2003 | Kisilevsky et al. | |
| 2003/0114441 A1 | 6/2003 | Weaver et al. | |
| 2003/0153584 A1 | 8/2003 | Weaver et al. | |
| 2003/0194375 A1 | 10/2003 | Weaver et al. | |
| 2003/0229144 A1 | 12/2003 | Weaver et al. | |
| 2004/0006092 A1 | 1/2004 | Chalifour et al. | |
| 2004/0096453 A1 | 5/2004 | Kisilevsky et al. | |
| 2004/0138178 A1 | 7/2004 | Szarek et al. | |
| 2004/0208875 A1 | 10/2004 | Kisilevsky et al. | |
| 2004/0219603 A1* | 11/2004 | Devarajan et al. | 435/7.1 |
| 2004/0220138 A1 | 11/2004 | Gervais et al. | |
| 2004/0248876 A1 | 12/2004 | Szarek et al. | |
| 2005/0031651 A1 | 2/2005 | Gervais et al. | |
| 2005/0038000 A1 | 2/2005 | Kong et al. | |
| 2005/0048000 A1 | 3/2005 | Gervais et al. | |
| 2005/0143462 A1 | 6/2005 | Kong et al. | |
| 2005/0214294 A1 | 9/2005 | Flyvbjerg et al. | |
| 2006/0008917 A1 | 1/2006 | Campbell et al. | |
| 2006/0014752 A1 | 1/2006 | Weaver et al. | |
| 2006/0116347 A1 | 6/2006 | Kisilevsky et al. | |
| 2006/0135479 A1 | 6/2006 | Szarek et al. | |
| 2006/0167057 A1 | 7/2006 | Kong et al. | |
| 2006/0167095 A1 | 7/2006 | Kisilevsky et al. | |
| 2006/0183806 A1 | 8/2006 | Kong et al. | |
| 2006/0223855 A1 | 10/2006 | Kong et al. | |
| 2006/0252829 A1 | 11/2006 | Garceau et al. | |
| 2007/0010573 A1 | 1/2007 | Kong et al. | |
| 2007/0015737 A1 | 1/2007 | Clark et al. | |
| 2007/0021483 A1 | 1/2007 | Chalifour et al. | |
| 2007/0078082 A1 | 4/2007 | Kisilevsky et al. | |
| 2007/0265334 A1 | 11/2007 | Kisilevsky et al. | |
| 2008/0070862 A1 | 3/2008 | Laster et al. | |

FOREIGN PATENT DOCUMENTS

| | | |
|---|---|---|
| EP | 0119274 B1 | 9/1984 |
| EP | 0293974 B1 | 12/1988 |
| EP | 0309421 B1 | 3/1989 |
| EP | 0323416 | 7/1989 |
| EP | 0330353 B1 | 8/1989 |
| EP | 0405834 A2 | 1/1991 |
| EP | 0457265 B1 | 11/1991 |
| EP | 0464759 A2 | 1/1992 |
| EP | 0533352 A2 | 3/1993 |
| EP | 0797992 A2 | 10/1997 |
| EP | 0710483 B1 | 6/2001 |
| EP | 1181024 B1 | 2/2002 |
| EP | 1473032 A1 | 11/2004 |
| FR | 2437834 A | 6/1980 |
| FR | 2437834 W | 6/1980 |
| JP | 1-151514 A | 6/1989 |
| JP | 1-151514 W | 6/1989 |
| JP | 1-171638 A | 7/1989 |
| JP | 1-171638 W | 7/1989 |
| JP | 2-78620 A | 3/1990 |
| JP | 2-78620 W | 3/1990 |
| JP | 2-149341 A | 6/1990 |
| JP | 2-149341 W | 6/1990 |
| JP | 3-83921 A | 4/1991 |
| JP | 3-83921 W | 4/1991 |
| JP | 0413603 W | 1/1992 |
| JP | 0416303 A | 1/1992 |
| JP | 5-17471 A | 1/1993 |
| JP | 5-17471 W | 1/1993 |
| WO | WO 88/09171 A1 | 12/1988 |
| WO | WO 89/05646 A1 | 6/1989 |
| WO | WO 90/09789 A2 | 9/1990 |
| WO | WO 9114434 | 10/1991 |
| WO | WO 92/02248 A1 | 2/1992 |
| WO | WO 92/14456 A1 | 9/1992 |
| WO | WO 9303714 A2 | 3/1993 |
| WO | WO 93/10459 A1 | 5/1993 |
| WO | WO 93/11762 A1 | 6/1993 |
| WO | WO 93/24118 A1 | 12/1993 |
| WO | WO 94/00135 A1 | 1/1994 |
| WO | WO 94/01116 A1 | 1/1994 |
| WO | WO 94/22437 A2 | 10/1994 |
| WO | WO 95/01096 A1 | 1/1995 |
| WO | WO 96/04195 A1 | 2/1996 |
| WO | WO 96/28187 | 9/1996 |
| WO | WO 96/28187 A1 | 9/1996 |
| WO | WO 96/39129 A1 | 12/1996 |
| WO | WO 97/09445 A1 | 3/1997 |
| WO | WO 9908685 A1 | 2/1999 |
| WO | WO 9938498 A1 | 8/1999 |
| WO | WO 9940909 A1 | 8/1999 |
| WO | WO 9959571 A2 | 11/1999 |
| WO | WO 00/27807 A2 | 5/2000 |
| WO | WO 00/69444 A1 | 11/2000 |
| WO | WO 01/85093 A2 | 11/2001 |
| WO | WO 02/100417 A2 | 12/2002 |
| WO | WO 03/045947 A1 | 6/2003 |
| WO | WO 2004037234 A2 | 5/2004 |
| WO | WO 2004058258 A1 | 7/2004 |
| WO | WO 2004/113391 A2 | 12/2004 |
| WO | WO 2006/039709 A1 | 4/2006 |
| WO | WO 2006/121853 A1 | 11/2006 |
| WO | WO 2007/004072 A2 | 1/2007 |
| WO | WO 2007/125385 A2 | 11/2007 |

OTHER PUBLICATIONS

Giunti S. and al., Diabetic nephropathy: from mechanisms to rational therapies. Minerva Medica (2006), vol. 97, No. 3, pp. 241-262.

Williams M. and Tuttle K., The Next Generation of Diabetic Nephropathy Therapies: An Update. Advances in Chronic Kidney Disease (2005), vol. 12, No. 2, pp. 212-222.

Locatelli F. et al., The importance of diabetic nephropathy in current nephrological. Nephrol Dial Transplant (2003), vol. 18, pp. 1716-1725.

Navarro J. and Mora C., Diabetes, Inflammation, Proinflammatory Cytokines, and Diabetic Nephropathy. The Scientific World Journal (2006), vol. 6, pp. 908-917.

Giunti., et al; Diabetic nephropathy: from mechaniams to rational therapies; Minerva Med. (2006); 97:241-62.

Internationai Preliminary Report on Patentability dated Jun. 24, 2008 in application PCT/IB2006/004262 (0772244-0126-049/PCT1X).

Iternational Preliminary Report on Patentability dated Aug. 19, 2009 in application PCT/IB2007/004088 (072244-0126-049/PCT2X).

International Search Report dated Jan. 16, 2006 in application PCT/IB2006/004262 (072244-0126-049/PCT1X).

International Search Report dated Mar. 9, 2009 in application PCT/IB2007/004088 (072244-126-049/PCT2X).

Locatelli,, et al; The importance of diabetic nephropathy in current nephrological practice 24686; Nephrol Dial Transplant (2003); 18:1716-25.

Navarro, et al; Diabetes, inflammation, proinflammatory cytokines, and diabetic nephropathy; Scientific World Journal (2006);6:908-17.

Rosario, et al; Lipids and diabetic nepropathy; Curr Diab Rep (2006); 6:455-62.

Russell, Diabetic nephropathy in patients with type 1 diabetes mellitus, Nephrol Nurs J, (2006), 33:15-28.

US Office Acton dated Apr. 5, 2010 in U.S. Appl. No. 11/963,038.

US Office Action dated Aug. 21, 2009 in U.S. Appl. No. 11/963,038.

Williams, et al; The next generation of diabetic nephropathy therapies: an update, Adv. Chronic. Kidney Dis,; (2005); 12:212-22.

Wittman, et al; Prevention and treatment of diabetic nephropathy; Diabetes Res Clin Pract (2005); 68:S36-S42.

Axelrad, M.A. et al. "Further Characterization of Amyloid-Enhaning Factor," Laboratory Investigation, 47(2) :139-146, 1982.

Booth, DR. et al. "The genetic basis of autosomal dominant familial Mediterranean fever." QJM, 93(4):217-221, Apr. 2000.

Brissette, Louise et al. "Differential Induction of the Serum Amyloid A Gene Family in Response to an Inflammatory Agent and to Amyloid-enhancing Factor." The Journal of Biological Chemistry, 264(32):19327-19332, 1989.

Buee. L. et al. "Alzheimer's disease: binding of vascular and neuroblastoma heparan sulfate proteoglycans to Amyloid beta protein A4." Advances in the Biosciences, 87:217-218, 1993.

Caughey, B. "Scrapie associated PrP accumulation and its prevention: insight from a cell culture." British Medical Bulletin, 49(4):860-872, 1993.

Caughey, B. "Scrapie-associated PrP accumulation and agent replication: effects on sulphated glycosaminoglycan analogues." Phil. Trans. R. Soc. Lond. B., 343:399-404, 1994.

Caughey, B. "Sulfated Polyanion inhibition of Scrapie-Associated PrP Accumulation in Cultured Cells." Journal of Virology, 1993.

Caughey, B. et al. Binding of the Protease-Sensitive Form of Prion Proten PrP to Sulfated Glycosaminoglycan and Congo Red, Journal of Virology, 68(4):2135-2141, 1994.

Caughey, B. "Protease-resistant PrP accumulation and scrapie agent replication: a role for sulphated glycosaminoglycans?" Biochemical Society Transactions, 648th Meeting, Belfast, 22:163-167, 1994.

Colon, Wilfredo et al. "Partial Denaturation of Transthyretin is Sufficient for Amyloid Fibril Formation in Vitro." Biochemistry, 31:8654-8660, 1992.

Dow, Kimberly E. et al. "Effects of a 4-deoxy-L-threo-pentose, a novel carbohydrate, on neural cell proteoglycan synthesis and fuction." Biochimica et Biophysica Acta, 1156 :7-14, 1992.

Ehhlers, Bernhard et al. "Dextran Sulphate 500 Delays and Prevents Mouse Scrapie by Impairment of Agent Replication in Spleen." The Journal of General Virology, 65:1325-1330, 1984.

Final Rejection dated Feb. 9, 2009 in related U.S. Appl. No. 11/405,348, filed Apr. 17, 2006.

Final Rejection dated Nov. 23, 2009 in related U.S. Appl. No. 11/405,348, filed Apr. 17, 2006.

Fraser, Paul E. "Effects of Sulfate Ions on Alzheimer beta/A4 Peptide Assemblies: Implications for Amyloid Fibril-Proteoglycan Interactions." Journal of Neurochemistry, 59:1531-1540, 1992.

Garceau, D. et al. "A prospective analysis of demography, etiology, and clinical findings of AA amyloidosis patients enrolled in the international clinical phase II/III Fibrillex™ study." Slideshow, On behalf of Fibrillex™ Amyloidosis Secondary Trial (FAST) Group, 2004.

Garceau, D. et al. "Safety, Tolerability and Pharmacokinetic Profile of Fibrillex™ (Anti-AA Amyloid Agent) in Healthy and Renal Impaired Subjects." Amyloid, The Journal of Protein Folding Disorders, Abstracts of The IXth International Symposium on Amyloidosis, 8(Suppl.2):39, 3.1.5 Poster and Oral Presentation, 2001.

Gervais, Francine et al. "Proteoglycans and Amyloidogenic Proteins in Peripheral Amyloidosis." Current Medical Chemistry, 3:361-370, 2003.

Gervais, Francine. "Amyloid—Those Deadly Fibrils." Euro. Biopharm. Review, p. 40-42, 2001.

Hamazaki, Hideaki et al. "Calcium-dependent polymerization of human serum Amyloid P component is inhibited by heparin and dextran sulfate." Biochimica et Biophysica Acta, 998:231-235, 1989.

Hamazaki, Hideaki. "$Ca^{2+}$-mediated Association of Human Serum Amyloid P Component with Heparan Sulfate and Dermatan Sulfate." The Journal of Biological Chemistry, 262(4):1456-1460, 1987.

Hauck, W. et al. "A Prospective Analysis of Demography, Etiology, and Clinical Findings of AA Amyloidosis Patients Enrolled in the International Clinical Phase II/III Fibrillex™ Study." Amyloid and Amyloidosis, p. 179-180, 2005.

Hazenberg, B.P.C. et al. "Diagnostic and therapeutic approach of systemic amyloidosis." Neth. J. Med., 62:121-128, 2004.

Hirschfield. G.M. et al. "Amyloidosis: new strategies for treatment." The International Journal of Biochemistry & Cell Biology, 35:1608-1613, 2003.

International Search Report for Application No. PCT/IB2006/002540, dated May 16, 2007.

Kagan, D.Z. et al. "Congo Red Inhibition of Amylogenesis in Experimental Amyloidosis." Problemy Tuberkuleza, 40:72-74.

Kergueris, MF et al. "Pharmacokinetics of high-dose melphalan in adults: influence of renal function." Anticancer Res., 14(6A): 2379-2382, Nov.-Dec. 1994.

Kisilevsky, R. "A Critical Analysis of Postualted Pathogenetic Mechanism in Amyloidogenesis." Critical Reviews in Clinical Laboratory Sciences, 29(1):59-82, 1992.

Kisilevsky, R. "From arthritis to Alzheimer's disease: current on the pathogenesis of amyloidosis." Can. J. Physiol. Pharmacol., 65:1805-1815, 1987.

Kisilevsky, R. "Heparan Sulfate Proteoglycans in Amyloidogenesis: An Epiphenomenon, A Unique Factor, or the Tip of a More Fundamental Process?" Laboratory Investigation, 63(5):589-591, 1990.

Kisilevsky, R. "The Potential Significance of Sulphated Glycosaminoglycans as a Common Constituent of all Amyloids: or Perhaps, Amyloid is not a Misnomer." Medical Hypotheses, 26:231-236, 1988.

Kisilevsky, R. "Theme and Variations on a String of Amyloid," Neurobiology of Aging, 10:499-500, 1989.

Kisilevsky, Robert et al. "Arresting amyloids in vivo using small-molecule anionic sulphonates or sulphates: implications for Alzheimer's disease." Nature Medicine, 1(2): 143-148, 1995.

Kisilevsky, Robert et al. "Short-Chain Aliphatic Polysulfonates Inhibit the Entry of Plasmodium into Red Blood Cells." Antimicrobial Agents and Chemotherapy, 46(8): 2619-2626, 2002.

Leveugle, B. et al. "Binding of heparan sulfate glycosaminoglycan to avoid beta-amyloid peptide: inhibition by potentially therapeutic polysulfated compounds." NeuroReport, 5:1389-1392, 1994.

Lyon, A.W. et al. "Co-deposition of Basement Membrane Components during the induction of Murine Splenic AA Amyloid." Laboratory Investigations, 64(6):785-790, 1991.

McCubbin, William D. et al. "Circular-dichroism studies on two murine serum Amyloid A proteins." Biochem. J. 256:775-783, 1988.

Miyazawa, Keisuke et al. "Occurrence of d-2-Hydroxy-3-aminopropane Sulfonic Acid and 3-Aminopropane Sulfonic Acid in a Red Alga Grateloupia lividia." Bulletin of Japanese Society of Scientific Fisheries, 36(1): 109-114, 1970.

Nakada, Tsutomu et al. "Guanidinoethane sulfate: brain pH alkaline shifter." NeuroReport, 4:1035-1038, 1993.

Narindrasorasak, Suree et al. "High Affinity Interactions between the Alzheimer's Beta-Amyloid Precursor Proteins and the Basement Membrane Form of Heparan Sulfate Proteoglycan." The Journal of Biological Chemistry, 226(20): 12878-12883, 1991.

Neurochem Inc. announces completion of Phase II/III clinical trial for Fibrillex™. Neurochem Press Release, Dec. 7, 2004.

Neurochem Inc. announces the signing of exclusive collaboration and distribution agreement for Fibrillex™ with Centocor, Inc., Neurochem Press Release, Dec. 22, 2004.

Neurochem Inc. unblinds the Phase II/III Clinical Study for Fibrillex™ in the treatment of AA Amyloidosis, Neurchem Press Release, Apr. 8, 2005.

Nomura, Shinsuke et al. "Amyloidosis (AA type) with Gastrointestinal Involvement: Resolution of Gastric Amyloid Deposition in Parallel with Disappearance of the Serum Component of Amyloid A Protein." Jpn. J. Med., 29(2), Mar.-Apr. 1990.

Non-Final Rejection dated Aug. 11, 2009 in related U.S. Appl. No. 11/405,348, filed Apr. 17, 2006.

Non-Final Rejection dated Aug. 21, 2009 in related U.S. Appl. No. 11/963,038, filed Dec. 21, 2007.

Non-Final Rejection dated Aug. 5, 2008 in related U.S. Appl. No. 11/405,348, filed Apr. 17, 2006.

Non-Final Rejection dated Oct. 15, 2007 in related U.S. Appl. No. 11/405,348, filed Apr. 17, 2006.

Ono, Kenjiro et al. "Nordihydroguaiaretic acid potently breaks down pre-formed Alzheimer's Beta-amyloid fibrils in vitro." Journal of Neurochemistry, 81:434-400, 2002.

Pollack, Scott J. et al. "Sulfonated dyes attenuate the toxic effects of Beta-amyloid in a structure-specific fashion." Neuroscience Letters, 197:211-214, 1995.

Puchtler, H. et al. "Application of Thiazole Dyes to Amyloid under Conditions of Direct Cotton Dyeing: Correlation of Histochemical and Chemical Data." Histochemistry, 77:431-445, 1983.

Related U.S. Appl. No. 11/405,348, filed Apr. 17, 2006.

Related U.S. Appl. No. 11/963,038, filed Dec. 21, 2007.

Revill, P. et al. "Eprodisate Sodium." Drugs of the Future, 31(7): 576-578, 2006.

Sadler, Isobel I.J. et al. "Sulphated compounds attenuate Beta-amyloid toxicity by inhibiting its association with cells." NeuroReport, 7:49-53, 1995.

Shue, Ho-Jane et al. "A Study of 3-Amino-N-Hydroxypropanesulfonamide Derivatives as Potential $GABA_B$ Agonists and Their Fragmentation to 3-Aminopropanesulfinic Acid." Bioorganic & Medicinal Chemistry Letters, 6(14): 1709-1714, 1996.

Small, D.H. et al. "Association and Release of the Amyloid Protein Precursor of Alzheimer's Disease from Chick Brain Extracellular Matrix." The Journal of Neuroscience, 12(11): 4143-4150, 1992.

Snow, Alan David et al. "A Close Ultrastructural Relationship between Sulfated Proteoglycans and AA Amyloid Fibrils." Laboratory Investigation, 57(6): 687-698, 1987.

Snow, Alan David et al. "A Temporal and Ultrastructural Relationship Between Heparan Sulfate Proteoglycans and AA Amyloid in Experimental Amyloidosis." The Journal of Histochemistry and Cytochemistry, 39(10): 1321-1330, 1991.

Snow, Alan David et al. "Characterization of Tissue and Plasma Glycosaminoglycans during Experimental AA Amyloidosis and Acute Inflammation, Qualitative and Quantitative Analysis." Laboratory Investigation, 56(1): 120-123, 1987.

Snow, Alan David et al. "Sulfated Glycosaminoglycans in Alzheimer's Disease." Human Pathology, 18(5): 506-510, 1987.

Snow, Alan David et al. "Sulfated glycosminoglycans in Amyloid plaques of prion diseases." Acta Neuropathol. 77:337-342, 1989.

Snow, Alan David et al. Temporal Relationship between Glycosaminoglycan Accumulation and Amyloid Deposition during Experimental Amyloidosis. Laboratory Investigation, 53(1):37-44, 1985.

Tape, C. et al. "Direct Evidence for Circulating apoSAA as the Precursor of Tissue AA Amyloid Deposits." Scand. J. Immunol., 28:317-324, 1988.

The Merck Index, p. 883, Merck & Co. Inc., Rahway, New Jersey, 1993.

Travis, John. "New Piece of Alzheimer's Puzzle." Science, 261: 828-829, 1993.

Tsuchiya, Teruo et al. "Antidotes for Paraquat Poisonings X: The Effect of Sulfonates and Sulfates on Absorption of Paraquat from Intestine." Jpn. J. Forensic. Toxicol. 9:130-131, 1991.

Wong, S. "Influence of Sulphate Ions on the Structure of AA Amyloid Fibrils." Scand. J, Immunol. 32: 225-232, 1990.

Wood, Stephen J. et al. "Selective Inhibition of a Beta Fibril Formation." The Journal of Biological Chemistry, 271(8): 4086-4092, 1996.

Young, Iain D. et al. "Localization of the Basement Membrane Heparan Sulfate Proteoglycan in Islet Amyloid Deposits in Type II Diabetes Mellitus." Arch Pathol Lab Med., 116: 951-954, 1992.

Young, Iain D. et al. "The ultrastructural localization of sulphated proteoglycans is identical in the amyloids of Alzheimer's disease and AA, AL, senile cardiac and medullary carcinoma-associated Amyloidosis." Acta Neuropathol. 78:202-209, 1989.

\* cited by examiner

TREATMENT OF RENAL DISORDERS, DIABETIC NEPHROPATHY AND DYSLIPIDEMIAS

RELATED APPLICATION

This application claims priority to U.S. provisional patent application No. 60/753,072 filed Dec. 22, 2005, which is incorporated herein by reference.

FIELD OF THE INVENTION

The invention relates to methods, compounds, and compositions for preventing, or treating renal disorders or chronic kidney diseases, including nephropathies such as diabetic nephropathy. The invention also relates to methods, compounds, and compositions for preventing or treating renal disorder complications. The invention further relates to methods, compounds, and compositions for the prevention and/or treatment of dyslipidemias, a common complication of renal disorders, chronic kidney diseases, and nephropathy.

BACKGROUND OF THE INVENTION

Renal disorders involve an alteration in the normal physiology and function of the kidney. Renal disorders can result from a wide range of acute and chronic conditions and events, including physical, chemical, or biological injury, insult or trauma, disease such as, for example, hypertension, diabetes, congestive heart failure, lupus, sickle cell anemia, and various inflammatory and autoimmune diseases, HIV-associated nephropathies, etc. Renal disorders can lead to reduced kidney function, hypertension, and renal failure, seriously compromising quality of life, sometimes requiring dialysis and in certain circumstances, kidney transplantation.

Diabetic nephropathy also known as Kimmelstiel-Wilson syndrome and intercapillary glomerulonephritis, is a progressive kidney disease caused by angiopathy of capillaries in the kidney glomeruli. It is characterized by nodular glomerulosclerosis due to longstanding diabetes mellitus and is a prime cause for dialysis in many Western countries. The syndrome can be seen in patients with chronic diabetes. The disease is progressive and may cause death two or three years after the initial lesions and is more frequent in women. Diabetic nephropathy is the most common cause of chronic kidney failure and end-stage kidney disease in the United States. People with both type 1 and type 2 diabetes are at risk. The risk is higher if blood-glucose levels are poorly controlled. However, once nephropathy develops, the greatest rate of progression is seen in patients with poor control of their blood pressure.

Diabetic nephropathy is clinically well defined and is characterized by proteinuria, hypertension, edema and renal insufficiency. There are limited treatment options for diabetic nephropathy. Current treatments are primarily directed to improving complications of the diseases as follows: 1) control of blood-pressure (ACE-inhibitors inhibitors or Angiotensin receptor blockers (ARBs); 2) Control of glycemic values; and 3) lipoproteic diet, exercise or other life styles modifications. However, there is an important need for better drugs and treatments since current treatment may have limited impact on the progressive decline in kidney function and patients still progress to renal replacement therapy, either dialysis or renal transplantation.

Hyperlipidemia is a major complication of diabetic nephropathy and is a determinant of progression of renal disorder in diabetes. Hyperlipidemia is a pathogenic factor for diabetic nephropathy and clinical studies involving therapeutic interventions for hyperlipidemia suggest the importance of this approach in at least slowing the progression of diabetic renal disorder (Rosario and Prabhakar (2006), *Current Diabetes Reports*, 6:455-462). Therefore, there is a need for methods and compounds for modulating blood lipids levels, and more particularly reducing levels of harmful serum lipid levels, especially cholesterol and triglycerides in diabetic patients.

SUMMARY OF THE INVENTION

The present invention provides compounds, methods and pharmaceutical compositions for preventing and/or treating renal disorder in a subject in need thereof.

The present invention further relates to methods, compounds and compositions for preventing and/or treating severity of a renal disorder complication.

The invention further relates to methods, compounds and compositions for the prevention and/or treatment of dyslipidemia, and more particularly for reducing serum levels of lipids involved in renal disorder complications, vascular and cardiovascular diseases, obesity and the like.

In one aspect, this invention relates to a method for preventing or treating diabetic nephropathy in a subject in need thereof, comprising administering to said subject 1,3-propanedisulfonic acid or a pharmaceutically acceptable salt thereof an effective amount of a compound of the Formula (I):

$$Y-(CH_2)_n-(CH)_t-[CH_2Y]_m \quad (I)$$

wherein Y is $SO_3X$ or $OSO_3X$ independently chosen for each occurrence; X is a cationic group which independently for each occurrence is hydrogen, lithium, sodium, potassium, calcium, magnesium, trialkylammonium or aluminum; n is 1, 2, 3 or 4; t is 0 when m is 1; and t is 1 when m is 2; wherein said subject does not have amyloidosis.

In another aspect, this invention relates to a method for preventing or treating a renal disorder complication in a subject in need thereof comprising administering to said subject an effective amount of a compound of the Formula (I):

$$Y-(CH_2)_n-(CH)_t-[CH_2Y]_m \quad (I)$$

wherein Y is $SO_3X$ or $OSO_3X$ independently chosen for each occurrence; X is a cationic group which independently for each occurrence is hydrogen, lithium, sodium, potassium, calcium, magnesium, trialkylammonium or aluminum; n is 1, 2, 3 or 4; t is 0 when m is 1; and t is 1 when m is 2; wherein said subject does not have amyloidosis.

In another aspect, this invention relates to a method for the prevention or treatment of dyslipidemia in a subject in need thereof, comprising administering to said subject an effective amount of a compound of the Formula (I):

$$Y-(CH_2)_n-(CH)_t-[CH_2Y]_m \quad (I)$$

wherein Y is $SO_3X$ or $OSO_3X$ independently chosen for each occurrence; X is a cationic group which independently for each occurrence is hydrogen, lithium, sodium, potassium, calcium, magnesium, trialkylammonium or aluminum; n is 1, 2, 3 or 4; t is 0 when m is 1; and t is 1 when m is 2.

In another aspect, this invention relates to a method of reducing serum lipid levels in a subject in need thereof comprising administering to said subject an effective amount of a compound of the Formula (I):

$$Y-(CH_2)_n-(CH)_t-[CH_2Y]_m \quad (I)$$

wherein Y is $SO_3X$ or $OSO_3X$ independently chosen for each occurrence; X is a cationic group which independently for each occurrence is hydrogen, lithium, sodium, potassium, calcium, magnesium, trialkylammonium or aluminum; n is 1, 2, 3 or 4; t is 0 when m is 1; and t is 1 when m is 2.

In another aspect, this invention relates to a method of increasing creatinine clearance in a subject in need thereof comprising administering to said subject an effective amount of a compound of the Formula (I):

$$Y—(CH_2)_n—(CH)_t—[CH_2Y]_m \quad (I)$$

wherein Y is SO₃X or OSO₃X independently chosen for each occurrence; X is a cationic group which independently for each occurrence is hydrogen, lithium, sodium, potassium, calcium, magnesium, trialkylammonium or aluminum; n is 1, 2, 3 or 4; t is 0 when m is 1; and t is 1 when m is 2; wherein said subject does not have amyloidosis.

In another aspect, this invention relates to a method of decreasing serum uric acid levels in a subject in need thereof comprising administering to said subject an effective amount of a compound of the Formula (I):

$$Y—(CH_2)_n—(CH)_t—[CH_2Y]_m \quad (I)$$

wherein Y is SO₃X or OSO₃X independently chosen for each occurrence; X is a cationic group which independently for each occurrence is hydrogen, lithium, sodium, potassium, calcium, magnesium, trialkylammonium or aluminum; n is 1, 2, 3 or 4; t is 0 when m is 1; and t is 1 when m is 2; wherein said subject does not have amyloidosis.

In another aspect, this invention relates to a method for improving kidney function in a human subject in need thereof, comprising administering to said subject an effective amount of a compound of the Formula (I):

$$Y—(CH_2)_n—(CH)_t—[CH_2Y]_m \quad (I)$$

wherein Y is SO₃X or OSO₃X independently chosen for each occurrence; X is a cationic group which independently for each occurrence is hydrogen, lithium, sodium, potassium, calcium, magnesium, trialklammonium or aluminum; n is 1, 2, 3 or 4; t is 0 when m is 1; and t is 1 when m is 2; wherein said subject does not have amyloidosis.

In another aspect, this invention relates to a method for preventing or treating diabetic nephropathy in a subject in need thereof, comprising administering to said subject 1,3-propanedisulfonic acid or a pharmaceutically acceptable salt thereof, wherein said subject does not have amyloidosis.

In some embodiments, the invention pertains to methods and pharmaceutical compositions comprising the use of a therapeutically effective amount of a compound of the formula:

$$Y—(CH_2)_n—(CH)_t—[CH_2Y]_m \quad (I)$$

wherein Y is SO₃X or OSO₃X independently chosen for each occurrence; X is a cationic group independently selected for each occurrence from the group consisting of hydrogen, lithium, sodium, potassium, calcium, magnesium, trialkylammonium and aluminum; n is 1, 2, 3 or 4; t is 0 when m is 1; and t is 1 when m is 2, such that the nephropathy is treated or prevented. In a preferred embodiment the compound of formula (I) is 1,3-propanedisulfonic acid or a pharmaceutically acceptable salt thereof, e.g. a disodium salt.

In some embodiments, the invention pertains to methods and pharmaceutical compositions comprising the use of a therapeutically effective amount of a compound selected from the group consisting of 1,2-ethanedisulfonic acid, 1,2-ethanediol bis(hydrogen sulfate), 1,3-propanediol bis(hydrogen sulfate), 2-sulfomethyl-1,4-butanedisulfonic acid, and pharmaceutically acceptable salts thereof.

The invention also pertains, at least in part, to a method for treating diabetic nephropathy in a subject. The method includes administering to a subject a therapeutically effective amount of a compound of formula (I), e.g., 1,3-propanedisulfonic acid or a pharmaceutically acceptable salt thereof, e.g. a disodium salt.

The invention also pertains to compounds, methods and compositions for the prevention and/or treatment of blood lipids-associated conditions by the administration of a compound of Formula (I) to a patient in need of such treatment.

The invention also pertains to compounds, methods and compositions for improving a kidney function of a subject in need thereof.

In another embodiment, the invention pertains, at least in part, to a method for preventing or delaying progression to end stage renal failure (ESRF)/dialysis in a subject having nephropathy, e.g. diabetic nephropathy. The method includes administering to the subject a therapeutically effective amount of a compound of formula (I), e.g., 1,3-propanedisulfonic acid or a pharmaceutically acceptable salt thereof, e.g. a disodium salt, such that progression to ESRF/dialysis is delayed or prevented.

In another embodiment, the invention pertains, at least in part, to a method for preventing or delaying the time to the doubling of serum creatinine in a subject having nephropathy, e.g. diabetic nephropathy. The method includes administering to the subject a therapeutically effective amount of a compound of formula (I), e.g., 1,3-propanedisulfonic acid or a pharmaceutically acceptable salt thereof, e.g. a disodium salt, such that the time to the doubling of serum creatinine is delayed or prevented.

In yet another embodiment, the invention pertains, at least in part, to a method for preventing or delaying the time to at least a 50% decrease in creatinine clearance in a subject having nephropathy, e.g. diabetic nephropathy. The method includes administering to a subject a therapeutically effective amount of a compound of formula (I), e.g., 1,3-propanedisulfonic acid or a pharmaceutically acceptable salt thereof, e.g. a disodium salt, such that the time to the at least a 50% decrease in creatinine clearance is delayed or prevented.

In yet another embodiment, the invention includes a method for reducing the rate of progression of renal disorder as measured by the slope of creatinine clearance in a subject having nephropathy, e.g. diabetic nephropathy. The method includes administering to the subject a therapeutically effective amount of a compound of formula (I), e.g., 1,3-propanedisulfonic acid or a pharmaceutically acceptable salt thereof, e.g. a disodium salt, such that the rate of progression of renal disorder is reduced.

In another embodiment, the invention pertains, at least in part, to a method for stabilizing or reducing proteinuria and/or albuminuria in a subject having nephropathy, e.g. diabetic nephropathy. The method includes administering to the subject a therapeutically effective amount of a compound of formula (I), e.g., 1,3-propanedisulfonic acid or a pharmaceutically acceptable salt thereof, e.g. a disodium salt, such that the proteinuria and/or albuminuria in said subject is stabilized or reduced.

In yet another embodiment, the invention includes a method for stabilizing renal function or delaying progression of renal disorder in a subject having nephropathy, e.g. diabetic nephropathy. The method includes administering to the subject a therapeutically effective amount of a compound of formula (I), e.g., 1,3-propanedisulfonic acid or a pharmaceutically acceptable salt thereof, e.g. a disodium salt, such that renal function is stabilized or progression of the renal disorder is delayed.

The invention also pertains, at least in part, to a pharmaceutical composition for treating nephropathy, e.g. diabetic nephropathy, comprising a therapeutically effective amount of a compound of formula (I), e.g., 1,3-propanedisulfonic acid or a pharmaceutically acceptable salt thereof, e.g. a disodium salt.

DETAILED DESCRIPTION OF THE INVENTION

Figure 1:
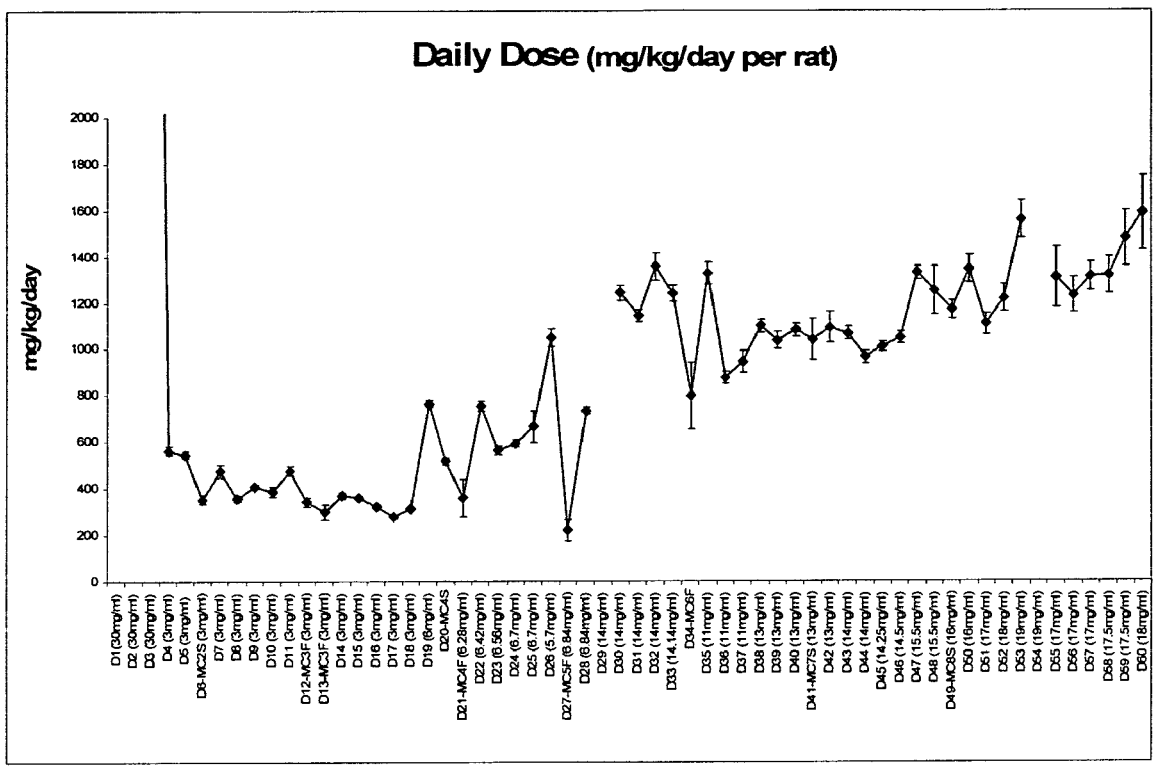
FIG. 1 is a line graph showing daily dose of 1,3-propanedisulfonic acid administered to Zucker diabetic obese male rats over a period of 60 days, according to Example 11.
Figure 2A:
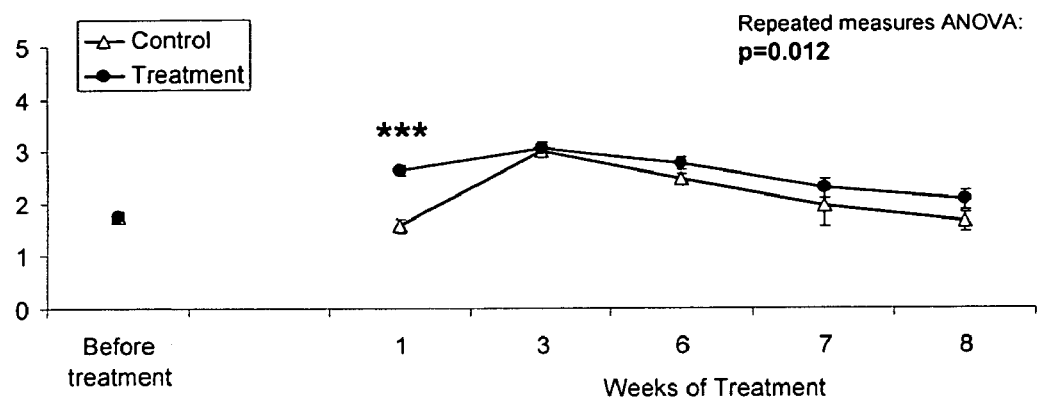
FIG. 2A is a line graph showing corrected creatinine clearance for control and treated satient Zucker diabetic obese male rats, over a period of 8 weeks, according to Example 11.
Figure 2B:
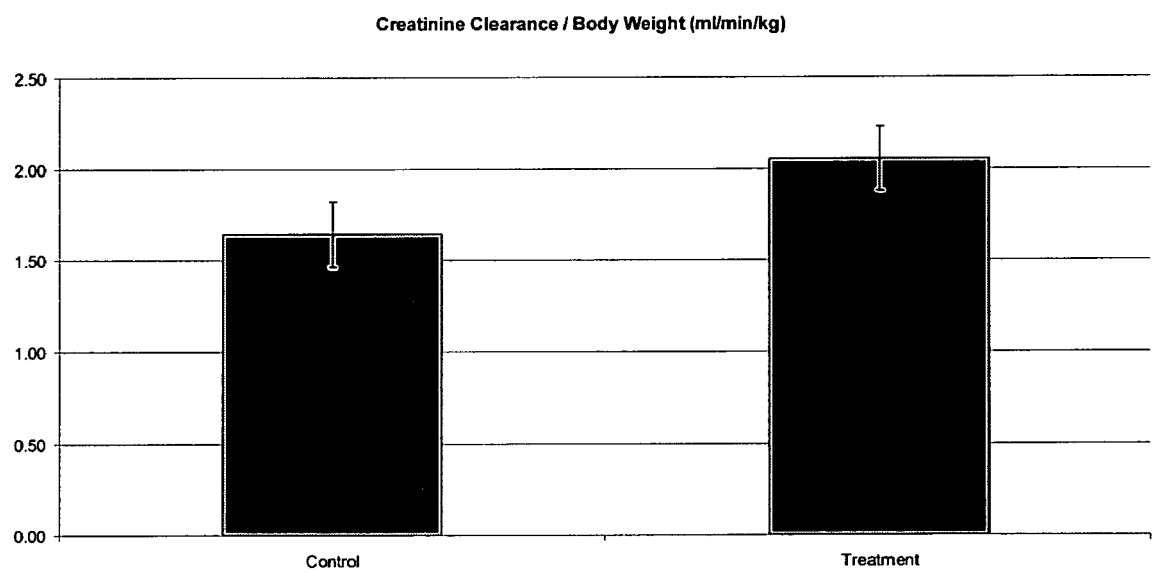
FIG. 2B is a bar graph showing corrected creatinine clearance for control and treated satient Zucker diabetic obese male rats at week 8.

In some aspects, the present invention relates to methods, compounds and compositions for preventing and/or treating a renal disorder in a subject in need thereof. The term "renal disorder", "renal disease" or "kidney disease" means any alteration in normal physiology and function of the kidney. This can result from a wide range of acute and chronic conditions and events, including physical, chemical or biological injury, insult, trauma or disease, such as for example hypertension, diabetes, congestive heart failure, lupus, sickle cell anemia and various inflammatory, infectious and autoimmune diseases, HIV-associated nephropathies etc. This term includes but is not limited to diseases and conditions such as kidney transplant, nephropathy; chronic kidney disease (CKD); Glomerulonephritis; inherited diseases such as polycystic kidney disease; nephromegaly (extreme hypertrophy of one or both kidneys); nephrotic syndrome; end stage renal disease (ESRD); acute and chronic renal failure; interstitial disease; nephritis; sclerosis, an induration or hardening of tissues and/or vessels resulting from causes that include, for example, inflammation due to disease or injury; renal fibrosis and scarring; renal-associated proliferative disorders; and other primary or secondary nephrogenic conditions. Fibrosis associated with dialysis following kidney failure and catheter placement, e.g., peritoneal and vascular access fibrosis, is also included.

In some embodiment, the renal disorder or kidney disease may be generally defined as a "nephropathy" or "nephropathies". The terms "nephropathy" or "nephropathies" encompass all clinical-pathological changes in the kidney which may result in kidney fibrosis and/or glomerular diseases (e.g. glomerulosclerosis, glomerulonephritis) and/or chronic renal insufficiency, and can cause end stage renal disease and/or renal failure. Some aspects of the present invention relate to compositions and their uses for the prevention and/or treatment of hypertensive nephropathy, diabetic nephropathy, and other types of nephropathy such as analgesic nephropathy, immune-mediated glomerulopathies (e.g. IgA nephropathy or Berger's disease, lupus nephritis), ischemic nephropathy, HIV-associated nephropathy, membranous nephropathy, glomerulonephritis, glomerulosclerosis, radiocontrast media-induced nephropathy, toxic nephropathy, analgesic-induced nephrotoxicity, cisplatin nephropathy, transplant nephropathy, and other forms of glomerular abnormality or injury; glomerular capillary injury (tubular fibrosis). In some embodiments, the terms "nephropathy" or "nephropathies" refers specifically to a disorder or disease where there is either the presence of proteins (i.e. proteinuria) in the urine of a subject and/or the presence of renal insufficiency.

The term "fibrosis" refers to abnormal processing of fibrous tissue, or fibroid or fibrous degeneration. Fibrosis can result from various injuries or diseases, and can often result from chronic transplant rejection relating to the transplantation of various organs. Fibrosis typically involves the abnormal production, accumulation, or deposition of extracellular matrix components, including overproduction and increased deposition of, for example, collagen and fibronectin. As used herein, the terms "kidney fibrosis" or "renal fibrosis" or "fibrosis of the kidney" refer to diseases or disorders associated with the overproduction or abnormal deposition of extracellular matrix components, particularly collagen, leading to the degradation or impairment of kidney function.

According to preferred embodiments, the present invention concerns methods, compounds and compositions for preventing or treating diabetic nephropathy in a subject in need thereof. Diabetic nephropathy is a clinically well-defined pathology characterized by proteinuria, hypertension, edema and renal insufficiency. Characteristic aspects of diabetic nephropathy include glomerulosclerosis, modification of the vascular structure, and tubulointerstitial disease. The first clinical evidence of diabetic nephropathy is often the presence of albuminuria in the urine, e.g. microalbuminuria or macroalbuminuria.

Diabetic nephropathy is typically characterized by the following: 1) glomerulosclerosis, 2) modification of the vascular structure, mainly in the small arterioles and 3) tubulointerstitial disease. The most characteristic aspect of diabetic nephropathy is the glomerular injury, detectable by the enlargement of the mesangium and by the thickening of the basal membrane, which often looks like a diffuse cicatrisation of the whole glomerule. The first clinical evidence of diabetic nephropathy is the presence of albuminuria or proteinuria. One refers to microalbuminuria when the amount of albumin in the urine is less than or equal to <300 mg/day and proteinuria when the total amount of protein in the urine is greater than 1 g/day. Prevention, reduction or elimination of symptoms or complications of HIV-associated nephropathy in the context of the present invention refers to: prevention of HIV-associated nephropathy before it occurs (for example if the treatment begins with the manifestation of initial clinical indications of HIV such as decrease in CD4-bearing cells), elimination of established HIVAN altogether (as determined, for example, by the return of renal functions parameters to normal), or reduction in the undesired symptoms of the disease manifested by the decrease in the severity of an existing condition of HIVAN. The reduction in the undesired symptoms may be determined for example by the improvement in renal function as compared to the function prior to treatment. Such remediation may be evident in a delay in the onset of renal failure (including dialysis or transplant) or in a decrease in the rate of the deterioration of renal functions as determined for example by the slowing of the rate of the increase of proteinuria or slowing the rate of the rise in serum creatinine or by the fall in the parameter of creatinine clearance or GFR), or decrease in at least one symptom or complication caused by HIVAN including hospitalization rate or mortality.

The present invention further relates to methods, compounds and compositions for preventing and/or treating a renal disorder complication. The term "renal disorder complication" refers to a secondary condition correlated with a renal disorder, a health condition, an accident, or a negative reaction occurring during the course of a renal disorder that can become worse in its severity. A "renal disorder complication" is usually associated with increasing severity of the renal disease in the subjects suffering from symptoms or pathological changes, which can become widespread throughout the body or affecting other organ systems. As used herein, the term "renal disorder complication" encompasses, but is not limited to vascular diseases (e.g. hypertension, macrovascular complications, microvascular complications, etc.), cardiovascular diseases (e.g. arteriosclerosis, atherosclerosis, coronary artery disease, congestive heart failure, stroke, angina, ischemic heat disease, myocardial infarction, etc), diabetic dyslipidemia, hyperlipidemia (e.g. hypercholesterolemia, hypertriglyceridemia, hyperlipoproteinemia), metabolic syndrome, obesity, anemia, edema, pancreatitis, weak bones, poor nutritional health and nerve damage.

The present invention further relates to methods, compounds and compositions for the prevention and/or treatment of dyslipidemias. The term "dyslipidemias" or "dyslipidemia" encompass all clinical-pathological conditions or diseases that are directly or indirectly related to undesirably high or low levels, and/or undesirable ratios, of any circulating blood lipids and/or lipoproteins, including but not limited to levels and/or ratios of triglycerides, cholesterol, ApoB, LpA, high density lipoprotein (HDL), high-density lipoprotein cholesterol (HDLC), very low density lipoprotein cholesterol (VLDLC), low density lipoprotein cholesterol (LDLC), intermediate density lipoprotein cholesterol, low density lipoprotein (LDL), and free fatty acids.

The term dyslipidemia encompasses disorders of lipoprotein metabolism, including lipoprotein overproduction or deficiency, hyperlipidemia (e.g. hypercholesterolemia, hypertriglyceridemia, hyperlipoproteinemia, etc), diabetic dyslipidemia, and also other diseases and conditions wherein blood lipids levels are considered a pathogenic factor, including, but not limited to: vascular diseases (e.g. hypertension, macrovascular complications, microvascular complications, etc.), cardiovascular diseases (e.g. arteriosclerosis, atherosclerosis, coronary artery disease, congestive heart failure, stroke, angina, ischemic heat disease, myocardial infarction, etc), metabolic syndrome, and obesity.

In another aspect, the present invention relates to methods of preventing or treating nephropathies (e.g., diabetic nephropathy). The methods generally include administering to a subject a compound of the present invention as described herein. For example, in one embodiment, the compound is 1,3-propanedisulfonic acid or a pharmaceutically acceptable salt thereof.

In one embodiment, the nephropathy is diabetic nephropathy. In one embodiment, administration of a compound of the invention may result in improved kidney function. In one embodiment, administration of a compound of the invention may result in the lowering the urinary excretion of albumin. In another embodiment, administration of a compound of the invention may result in increased creatinine clearance and/or uric acid clearance.

In one embodiment, 1,3-propanedisulfonic acid and/or 1,3-propanedisulfonic acid sodium salt is administered to the subject.

The term "subject" includes living organisms in which renal disorders or nephropathy can occur, or which are susceptible to kidney disorder or nephropathy. The term "subject" includes animals (e.g., mammals, e.g., cats, dogs, horses, pigs, cows, goats, sheep, rodents, e.g., mice or rats, rabbits, squirrels, bears, primates (e.g., chimpanzees, monkeys, gorillas, and humans)), as well as chickens, ducks, Peking ducks, geese, and transgenic species thereof. Preferably, the subject is a mammal. More preferably, the subject is a human.

In some embodiments, the subject is a human patient having or susceptible of having glomerular filtration problems (e.g. diabetic nephropathy) and/or a renal failure. In some embodiments, the subject is a human patient having or susceptible to have a dyslipidemia, including but not limited to diabetic dyslipidemia, hyperlipidemia, vascular and cardiovascular diseases, metabolic syndrome X, and obesity.

In some embodiments, the subject may be suffering from a disorder such as, for example, diabetes, HIV, advanced progressive renal disease, and fibrotic renal disease and/or any of the diseases/disorders described herein. In one aspect the subject does not have amyloidosis. In one aspect the subject does not have Amyloid A (AA) amyloidosis. In another embodiment, the subject does have amyloidosis. In another embodiment, the subject does have Amyloid A (AA) amyloidosis.

In some embodiments the renal disease in not related to amyloid and the subject may or may not have amyloidosis (e.g. AA amyloidosis or IAPP-related amyloidosis). In some embodiments the nephropathy is not related to amyloid and the subject may or may not have amyloidosis (e.g. AA amyloidosis or IAPP-related amyloidosis). In some embodiments the diabetic nephropathy is not related to amyloid and the subject may or may not have amyloidosis (e.g. AA amyloidosis or IAPP-related amyloidosis). In some embodiments the renal disorder complication is not related to amyloid and the subject may or may not have amyloidosis (e.g. AA amyloidosis or IAPP-related amyloidosis). In a particular embodiment, in all the methods of this invention, the subject does not have amyloidosis (e.g. AA amyloidosis or IAPP-related amyloidosis). In a particular embodiment, in all the methods of this invention, the subject does not have AA amyloidosis. In a particular embodiment, in all the methods of this invention, the subject does not have IAPP-related amyloidosis. In some embodiments, the subject may be exhibiting proteinuria (e.g. microalbuminuria or macroalbuminuria). In some embodiments, the subject may have kidneys that have become less able to clear toxins from the blood, such as urea, uric acid and creatinine. In some embodiments, the methods, compounds or compositions of the invention are effective in slowing the decline in a patient's creatinine clearance by at least 0.5, 1, 2, 5, 10, 15, or 20 ml/min/1.73 m$^2$/year. In some embodiments, the methods, compounds or compositions of the invention are effective in stabilizing a patient's uric acid clearance by at least 1, 2, 5, 10, 15 or 20 mg/dL.

In some embodiments, the subject is at risk of, or has been diagnosed with, nephropathy, e.g. diabetic nephropathy. Typically a normal glomerular filtration rate (GFR) in humans is from about 100 to about 140 ml/min. In some embodiments, the subject is a human patient having advanced nephropathy (i.e. a GFR of under 75 ml/min). In some embodiments, the subject is a human patient having ESRD (i.e. GFR of less than 10 ml/min). In some embodiments, the methods, compounds or compositions of the invention are effective in increasing the patients' GFR value by at least 1, 5, 10, 15, 20 or 25, Iml/min or more.

In some embodiments, the subject is at risk of, or has been diagnosed with, a kidney disease. In various embodiments, the subject is a human patient having or progressing towards stage I kidney disease, stage II kidney disease, stage III kidney disease, stage IV kidney disease or stage V kidney disease. In some embodiments, the methods, compounds or compositions of the invention are effective in stabilizing or in improving the patient's kidney disease ((e.g. from stage V to stage IV, or from stage IV to stage III, or from stage III to stage II, or from stage II to stage I).

In some embodiments, the subject is at risk of, or has been diagnosed with, proteinuria. In some embodiments, the subject is a human patient producing less than about 300 mg/day of protein in its urine. In some embodiments, the subject is a human patient producing more that about 1 g/day of protein in its urine. In some embodiments, the subject is a human patient having microalbuminuria. In some embodiments, the subject is a human patient with albumin amount in the urine exceeds 200 μg/min. In some embodiments, the methods, compounds or compositions of the invention are effective in lowering the patients' albuminuria by at least 10, 25, 50, 75, 100, 150, 200 μg/min or more.

In some embodiments, the subject is at risk of, or has been diagnosed with, hypertension or high blood pressure. There is often a strong correlation between hypertension and kidney diseases such as nephropathy, particularly diabetic nephropathy. Individuals with poor kidney function frequently exhibit hypertension. In some embodiments, the subject is a hypertensive human patient having a systolic pressure of 140 mm Hg or higher and/or a diastolic pressure of 90 mm Hg or higher. In some embodiments, the subject is a prehypertensive human patient having a systolic pressure of about 120-139 mm Hg or higher and/or a diastolic pressure of 80-89 mm Hg or higher. In some embodiments, the methods, compounds or compositions of the invention are effective in lowering the patients' systolic and/or diastolic blood pressure by at least 1, 2, 3, 4, 5, 6, 7, 8, 9, 10 mm Hg or more.

In some embodiments, the subject is a hyperlipidemic human patient. In some embodiments, the levels of lipids in the blood are too high, and the compositions of the invention are administered to a patient to restore normal levels. Normal levels of lipids are reported in medical treatises known to those of skill in the art. For example, recommended blood levels of LDL, HDL, free triglycerides and others parameters relating to lipid metabolism can be found at the web site of the American Heart Association and that of the National Cholesterol Education Program of the National Heart, Lung and Blood Institute (see http://www.americanheart.org/ and http://www.nhlbi.nih.gov/health/public/heart/, respectively). In some embodiments, the subject is a hypercholesterolimic human patient having a plasma LDL cholesterol level over than 100 mg/dL and/or a plasma HDL cholesterol level of 40 mg/dL or lower. In some embodiments, the subject is a hypertriglycemic human patient having borderline-high plasma triglycerides level of 150 to 199 mg/dL, or high plasma triglycerides level of 200 to 499 mg/dL, or very high plasma triglycerides level of 500 mg/dL or higher. Those levels are based on measurement under fasting conditions. Elevated triglycerides are frequently found in association with kidney diseases and nephropathy, particularly diabetic nephropathy. In some embodiments, the methods, compounds or compositions of the invention are effective in lowering the patient's LDL cholesterol level and/or plasma triglycerides level by at least 5, 10, 15, 20, 30, 40, 50, 75, 100, 125, 150, 175, 200 mg/dL or more. In some embodiments, the methods, compounds or compositions of the invention are effective in increasing the patient's HDL cholesterol level and/or plasma triglycerides level by at least 1, 2, 5, 10, 15, 20, 25, 30 mg/dL or more. An example of successive treatment of hypercholesterolemia according to the invention is aimed at lowering human serum cholesterol levels to under 5.0 mmol/l.

In some embodiments, the subject is overweight or obese. In some embodiments, the subject is an obese human patient having a body mass index (BMI) of about 25 to 30 (grade 1), or a BMI of 30-40 (grade 2), or a BMI of over 40 (grade 3). In some embodiments, the methods, compounds or compositions of the invention are effective in reducing the patient's body mass index of a value of 1, 2, 5, 10, 15, 20, 25, 30, 35, 40 or more. In some embodiments, the methods, compounds or compositions of the invention are effective in improving the patient's BMI grade (e.g. from grade 3 to grade 2, or from grade 2 to grade 1).

In some embodiments, the subject is at risk of or has been diagnosed with metabolic syndrome (or syndrome X). In some embodiments, the subject is an human patient with presence of three or more of these components: elevated serum triglycerides (over 150 mg/dL), low HDL (under 40 mg/dl for men and under 50 mg/dl for women), increased waist circumference (over 102 cm in males and over 88 cm in females), Elevated blood pressure, and high fasting plasma glucose 100 mg/dl. In some embodiments, the methods, compounds or compositions of the invention are effective in losing any one of the above mentioned components of syndrome X.

In some embodiments, the subject is at risk of or has been diagnosed with diabetes. In some embodiments, the subject is a human patient with type 2 diabetes. In some embodiments, the subject is a human patient with type 1 diabetes.

In some embodiments the compound is administered to the subject in a pharmaceutical composition further comprising a pharmaceutically acceptable vehicle. In some embodiments, the method includes orally administering the pharmaceutical composition. In some embodiments, the method includes intravenously administering the pharmaceutical composition.

The terms "effective amount" or "therapeutically effective amount" are used interchangeably herein and refer to the amount of a compound which is effective to treat a subject, e.g., treat a subject for nephropathy (e.g., diabetic nephropathy), and/or a related complication or treat a subject having an underlying disease. The therapeutically effective amount may vary based on the particular disorder(s) the subject is suffering from, the age, weight, and lifestyle of a particular subject. In addition, the therapeutically effective amount may depend on the subject's blood parameters (e.g. lipid profile), the severity of the disease state, organ function, kidney function, or underlying disease or complications.

For example, the therapeutically effective amount of the compound of formula (I) may be between about 100 and 4000 mg daily. The compounds of the invention may be manufactured in tablets, pills, or capsules with dosages of 200 mg, 400 mg, or 800 mg, or 1200 mg or 1800 mg of the compound of the invention. In some embodiments, a therapeutically effective amount may be 400 mg BID, 800 mg BID, 1200 mg, 1600 mg, 2400 mg or 3600 mg BID. BID means twice a day. In some embodiments, a therapeutically effective amount is aimed at obtaining serum levels in human patients corresponding to at least 1, 5, 10, 25, 50, 75, or 100 μg/ml. As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). In some embodiments, the subject candidate for preventive treatment is a patient at risk of, a patient whom has been diagnosed with, or whom is progressing towards a renal disorder, a renal disorder complication, a vascular or a cardiovascular disease, diabetes, obesity and the like. Biological and physiological parameters for identifying such patients are provided herein and are also well known by physicians.

The terms "treatment" or "treating" of a subject includes the application or administration of a compound of the invention to a subject (or application or administration of a compound of the invention to a cell or tissue from a subject) with the purpose of stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being. For example, quantitative assessment of renal function and parameters of renal dysfunction are well known in the art and examples of assays for the determination of renal function/dysfunction are given hereinafter and includes evaluating at least one kidney function as assessed using biological and/or physiological parameters such as serum creatinine level, creatinine clearance rate, 24-hour urinary protein secretion, glomerular filtration rate, urinary albumin creatinine ratio, albumin excretion rate, and renal biopsy. In an embodiment, the term "treating" can include increasing a subject's life expectancy and/or delay before dialysis or kidney transplantation is required.

In some embodiments the invention pertains to pharmaceutical compositions for treating nephropathy, e.g., diabetic nephropathy, that include one or more compounds of formula (I):

$$Y-(CH_2)_n-(CH)_t-[CH_2Y]_m \quad (I)$$

wherein Y is $SO_3X$ or $OSO_3X$ independently chosen for each occurrence; X is a cationic group independently selected for each occurrence; n is 1, 2, 3 or 4; t is 0 when m is 1; and t is 1 when m is 2. The term "cationic group" includes groups with a positive charge and hydrogen atoms. Examples of cations include pharmaceutically acceptable salts of the $SO_3^-$ or $OSO_3^-$. Examples of cationic groups include ions of alkali or alkaline earth metals, such as lithium, sodium, potassium, calcium, magnesium, trialkylammonium and aluminum and the like. In a further embodiment, the cationic groups are $H^+$ or $Na^+$.

Examples of compounds of the invention include the compounds in the following table and pharmaceutically acceptable salts thereof.

| | |
|---|---|
| 1,2-Ethanedisulfonic acid | $HO_3SCH_2CH_2SO_3H$ |
| Sodium 1,2-ethanedisulfonate | $NaO_3SCH_2CH_2SO_3NA$ |
| 1,3-propanedisulfonic acid | $HO_3SCH_2CH_2CH_2SO_3H$ |
| Sodium 1,3-propanedisulfonate (1,3-propanedisulfonic acid, disodium salt) | $NaO_3SCH_2CH_2CH_2SO_3Na$ |
| 1,2-Ethanediol bis(hydrogen sulfate) | $HO_3SOCH_2CH_2OSO_3H$ |
| 1,2-Ethanediol disulfate, disodium salt | $NaO_3SOCH_2CH_2OSO_3Na$ |
| 1,3-Propanediol bis(hydrogen sulfate) | $HO_3SOCH_2CH_2CH_2OSO_3H$ |
| 1,3-Propanediol disulfate, disodium salt | $NaO_3SOCH_2CH_2CH_2OSO_3Na$ |
| 2-Sulfomethyl-1,4-butanedisulfonic acid | $HO_3SCH_2CH_2CH(CH_2SO_3H)_2$ |
| 2-Sulfomethylbutane-1,4-disulfonic acid, trisodium salt | $NaO_3SCH_2CH_2CH(CH_2SO_3Na)_2$ |

The term "compound" includes chemical entities. The compounds may be in solid, liquid or gaseous phase. The term compound includes the compounds of formula (I) and pharmaceutically acceptable salts thereof. Compounds of the invention are identified herein by their chemical structure and/or chemical name. Where a compound is referred to by both a chemical structure and a chemical name, and that chemical structure and chemical name conflict, the chemical structure is determinative of the compound's identity. The compounds of the invention may contain a chiral center and, therefore, may exist as stereoisomers. Compounds, as defined herein, may be purified from natural sources, purchased from commercial sources or chemically synthesized using art recognized techniques.

In general, all compounds of the present invention may be prepared by any conventional methods, using readily available and/or conventionally preparable starting materials, reagents and conventional synthesis procedures. More particularly, 1,3-propanedisulfonic acid or a pharmaceutically acceptable salt thereof may be prepared by the methods described in U.S. Pat. No. 5,643,562 In addition, the compounds of the invention also may exist in hydrated and anhydrous forms. Hydrates of the compound of formula (I) are included as compounds of formula (I). In a further embodiment, the compound of formula (I) is a monohydrate. In one embodiment, the compound of formula (I) comprises about 10% or less, about 9% or less, about 8% or less, about 7% or less, about 6% or less, about 5% or less, about 4% or less, about 3% or less, about 2% or less, about 1% or less, about 0.5% or less, about 0.1% or less by weight of water. In another embodiment, the compounds of the invention comprise, about 0.1% or more, about 0.5% or more, about 1% or more, about 2% or more, about 3% or more, about 4% or more, about 5% or more, or about 6% or more by weight of water.

In addition, the compounds of the invention may also encompass more than one polymorphic forms, hydrated states, etc. For example, one form, Form I, can be prepared by direct recrystallization of a compound of the invention, e.g., 1,3-propanedisulfonic acid, disodium salt. The compound is precipitated from solution with 16:1 ethanol:water (v/v). The recrystallized product is recovered as a fine white powder which is then dried at 65° C. for 16 hours at 4 mm Hg. The resulting non-hydrated form has a moisture content of 0.2% and an apparent density of 0.64 g/ml. In a further embodiment, the compound of formula (I) has a moisture content of about 0.2%.

Furthermore, another form, Form II, can be prepared by direct recrystallization of a commercially available 1,3-propanedisulfonic acid, disodium salt in a fashion similar to Form I. The compound is precipitated from solution with 8:1 ethanol:water (v/v). The recrystallized product is recovered as a white solid which is then dried at 20-25° C. for 16 hours at 4 mm Hg. The resulting mono-hydrated form has a moisture content of about 7% w/w and an apparent density of 0.46 g/ml. In a further embodiment, the compound of formula (I) has a moisture content of about 7%.

Form I can be also be prepared from the Form II polymorph by prolonged heating at reduced pressures. First, the Form II polymorph (water content 6.8%) is dried at 65° C. for 16 hours in a vacuum at 4 mm Hg. This initial drying reduces the water content of the formerly hydrated polymorph to 2.3%. After another 24 hours at 65° C., the moisture content of the formerly monohydrated polymorph is reduced to 1%. The compound is entirely converted to Form I polymorph only after an additional 48 hours of drying at 77° C.

The compounds of the present invention contain one or more acidic functional groups and, thus, are capable of forming pharmaceutically acceptable salts with pharmaceutically acceptable bases. A "pharmaceutically acceptable salt" of a compound means a salt of a compound that is pharmaceutically acceptable. Desirable are salts of a compound that retain or improve the biological effectiveness and properties of the free acids and bases of the parent compound as defined herein, or that takes advantage of an intrinsically basic, acidic or charged functionality on the molecule and that is not biologically or otherwise undesirable. Example of pharmaceutically acceptable salts are also described, for example, in Berge et al., "Pharmaceutical Salts", *J. Pharm. Sci.* 66, 1-19 (1977). Such salts include base addition salts, formed when an acidic proton present in the parent compound either is replaced by a metal ion, including, an alkali metal ion (e.g. lithium, sodium, potassium), an alkaline earth ion (e.g. magnesium, calcium, barium), or other metal ions such as aluminum, zinc, iron and the like; or coordinates with an organic base such as ammonia, ethylamine, diethylamine, ethylenediamine, N,N'-dibenzylethylenediamine, ethanolamine, diethanolamine, triethanolamine, trialkylamine (e.g. with a $C_1$-$C_4$ alkyl), tromethamine, N-methylglucamine, piperazine, chloroprocain, procain, choline, lysine and the like.

Pharmaceutically acceptable salts may be synthesized from the parent agent that contains an acidic moiety, by conventional chemical methods. Generally, such salts are prepared by reacting the free acid forms of these agents with a stoichiometric amount of the appropriate base in water or in an organic solvent, or in a mixture of the two. Salts may be prepared in situ, during the final isolation or purification of the agent or by separately reacting a purified compound of the invention in its free acid form with the desired corresponding base, and isolating the salt thus formed.

All acid, salt and other ionic and non-ionic forms of the compounds described are included as compounds of the invention. For example, if a compound is shown as an acid herein, the salt forms of the compound are also included. Likewise, if a compound is shown as a salt and the acid forms are also included.

In a further embodiment, the compound of formula (I) is not 1,3-propanedisulfonic acid disodium salt or 1,3-propanedisulfonic acid.

In a further embodiment, compounds of the invention include compounds disclosed in WO 94/22437[s/1], WO 96/28187[s/2], and WO 00/64420[t/3], the contents of which are hereby incorporated by reference in their entirety.

In a further embodiment, the composition or formulation is not as described in Example 1 or as described in any of the examples. In another further embodiment, at least one ingredient is not an ingredient described in Example 1 or as described in any of the examples.

Pharmaceutical Compositions

A related aspect of the invention concerns pharmaceutical compositions for use: (i) in preventing or treating renal disorders and more particularly nephropathy, (ii) in preventing or treating renal disorder complications and/or (iii) prevention and/or treatment of dyslipidemias.

A related aspect of the invention concerns the use of a compound of Formula (I) as described herein, preferably 1,3-propanedisulfonic acid or a pharmaceutically acceptable salt thereof, and more preferably 1,3-propanedisulfonic acid sodium salt, in the manufacture of a medicament for use: (i) in preventing or treating a renal disorder and more particularly nephropathy, (ii) in preventing or treating renal disorder complications and/or (iii) prevention and/or treatment of dyslipidemias. As use herein, the terms "pharmaceutical composition" and "medicament" are used interchangeably.

In some embodiments, the compositions of the invention comprise an effective amount of a compound of the Formula (I) as described hereinbefore, preferably 1,3-propanedisulfonic acid or a pharmaceutically acceptable salt thereof, and more preferably 1,3-propanedisulfonic acid sodium salt.

Accordingly, in another embodiment, the present invention relates to pharmaceutical compositions comprising effective amounts of one or more compounds according to Formula (I) herein and a pharmaceutically acceptable vehicle, as well as methods of using and manufacturing such pharmaceutical compositions.

As used herein, the term "pharmaceutical composition" refers to at least one compound and at least one pharmaceutically acceptable vehicle, with which the compound is administered to a subject.

"Pharmaceutically acceptable vehicle" refers to a diluent, adjuvant, excipient, or carrier with which a compound is administered. The term "pharmaceutically acceptable" refers to drugs, medicaments, inert ingredients etc., which the term describes, suitable for use in contact with the tissues of humans and lower animals without undue toxicity, incompatibility, instability, irritation, allergic response, and the like, commensurate with a reasonable benefit/risk ratio. It preferably refers to a compound or composition that is approved or approvable by a regulatory agency of the Federal or state government or listed in the U.S. Pharmacopoeia or other generally recognized pharmacopoeia for use in animals and more particularly in humans.

As used herein, the term "therapeutically effective amount" means the amount of compound that, when administered to a subject for treating or preventing a disease, is sufficient to effect such treatment or prevention of the disease. As indicated hereinbefore, the "therapeutically effective amount" will vary depending on the compound, the disease and its severity, and the age, weight, etc., of the subject in need of treatment.

The compounds of the invention may be formulated prior to administration into pharmaceutical compositions using available techniques and procedures (e.g. US patent application No. US 2006/0252829, which is incorporated herein by reference). For instance, the pharmaceutical compositions are formulated into suitable administration (orally, parenterally, (IV, IM, depo-IM, SC, and depo SC), sublingually, intranasally (inhalation), intrathecally, topically, or rectally). Suitable pharmaceutically acceptable vehicles include, without limitation, any non-immunogenic pharmaceutical carrier or diluent suitable for oral, parenteral, nasal, mucosal, transdermal, topical, intrathecal, rectal, intravascular (IV), intraarterial (IA), intramuscular (IM), and subcutaneous (SC) administration routes, such as phosphate buffer saline (PBS). Also, the present invention includes such compounds which have been lyophilized and which may be reconstituted to form pharmaceutically acceptable formulations for administration, as by intravenous, intramuscular, or subcutaneous injection. Administration may also be intradermal or transdermal.

The vehicle can be a solvent or dispersion medium containing, for example, water, ethanol, polyol (for example, glycerol, propylene glycol, and liquid polyethylene glycol, and the like), suitable mixtures thereof, and vegetable oils.

The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Preferably, the compound(s) of the invention can be orally administered. Formulations of the present invention include those suitable for oral administration. The formulations may conveniently be presented in unit dosage form and may be prepared by any methods well known in the art of pharmacy. Methods of preparing these formulations or compositions include the step of bringing into association a compound of the present invention with a pharmaceutically acceptable vehicle (e.g. an inert diluent or an assimilable edible carrier) and, optionally, one or more accessory ingredients. In general, the formulations are prepared by uniformly and intimately bringing into association a compound of the present invention with liquid carriers, or finely divided solid carriers, or both, and then, if necessary, shaping the product. The amount of the therapeutic agent in such therapeutically useful compositions is such that a suitable dosage will be obtained.

Formulations of the invention suitable for oral administration may be in the form of capsules (e.g. hard or soft shell gelatin capsule), cachets, pills, tablets, lozenges, powders, granules, pellets, dragees, e.g., coated (e.g., enteric coated) or uncoated, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) or as mouth washes and the like, each containing a predetermined amount of a compound of the present invention as an active ingredient. A compound of the present invention may also be administered as a bolus, electuary or paste, or incorporated directly into the subject's diet. Moreover, in certain embodiments these pellets can be formulated to (a) provide for instant or rapid drug release (i.e., have no coating on them); (b) be coated, e.g., to provide for sustained drug release over time; or (c) be coated with an enteric coating for better gastrointestinal tolerability.

In solid dosage forms of the invention for oral administration the active ingredient is mixed with one or more pharmaceutically acceptable carriers, such as sodium citrate or dicalcium phosphate, or any of the following: fillers or extenders, such as starches, lactose, sucrose, glucose, mannitol, or silicic acid; binders, such as, for example, carboxymethylcellulose, alginates, gelatin, polyvinyl pyrrolidone, sucrose or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Peroral compositions typically include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the therapeutic agent) plus any additional desired ingredient from a previously sterile-filtered solution thereof.

Pharmaceutical formulations are also provided which are suitable for administration as an aerosol, by inhalation. These formulations comprise a solution or suspension of the desired compound of any Formula herein or a plurality of solid particles of such compound(s). The desired formulation may be placed in a small chamber and nebulized. Nebulization may be accomplished by compressed air or by ultrasonic energy to form a plurality of liquid droplets or solid particles comprising the agents or salts. The liquid droplets or solid particles should have a particle size in the range of about 0.5 to about 5 microns. The solid particles can be obtained by processing the solid agent of any Formula described herein, or a salt thereof, in any appropriate manner known in the art, such as by micronization. The size of the solid particles or droplets will be, for example, from about 1 to about 2 microns. In this respect, commercial nebulizers are available to achieve this purpose.

A pharmaceutical formulation suitable for administration as an aerosol may be in the form of a liquid, the formulation will comprise a water-soluble agent of any Formula described herein, or a salt thereof, in a carrier which comprises water. A surfactant may be present which lowers the surface tension of the formulation sufficiently to result in the formation of droplets within the desired size range when subjected to nebulization.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions may comprise an effective amount, usually at least about 0.1%, or even from about 1% to about 5%, of an agent of the invention. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emollients, emulsifiers, thickening agents, solvents and the like.

Other compositions useful for attaining systemic delivery of the subject agents include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included. The compound(s) of the invention may also be administered parenterally, intraperitoneally, intraspinally, or intracerebrally. For such compositions, the compound(s) of the invention can be prepared in glycerol, liquid polyethylene glycols, and mixtures thereof and in oils. Under ordinary conditions of storage and use, these preparations may contain a preservative to prevent the growth of microorganisms.

To administer the compound(s) of the invention by other than parenteral administration, it may be useful to coat the compound(s) with, or co-administer the compound(s) with a material to prevent its inactivation. For example, the compound(s) of the invention may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes.

Pharmaceutical compositions according to the invention may also be coated by conventional methods, typically with pH or time-dependent coatings, such that the compound(s) of the invention is released in the vicinity of the desired location, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

Dosage

It is understood that appropriate doses depend upon a number of factors within the knowledge of the ordinarily skilled physician, veterinarian, or researcher. The dose(s) of the compound(s) of the invention will vary, for example, depending upon a variety of factors including the activity of the specific agent employed, the age, body weight, general health, gender, and diet of the subject, the time of administration, the route of administration, the rate of excretion, and any drug combination, if applicable, the effect which the practitioner desires the compound to have upon the subject and the properties of the compounds (e.g. bioavailability, stability, potency, toxicity, etc). Such appropriate doses may be determined using any available assays including the assays described herein. When one or more of the compounds of the invention is to be administered to humans, a physician may for example, prescribe a relatively low dose at first, subsequently increasing the dose until an appropriate response is obtained.

For example, the therapeutically effective amount of the compound of formula (I) may be between about 100 and 4000 mg daily. The compounds of the invention may be manufactured in tablets, pills, or capsules with dosages of 200 mg, 400 mg, or 800 mg, or 1200 mg, or 1800 mg, or 2400 mg of the compound of the invention. In some embodiments, a therapeutically effective amount may be 400 mg BID, 800 mg BID, 1200 mg, 1600 mg, 2400 mg or 3600 mg BID. BID means twice a day. In some embodiments, a therapeutically effective is aimed at obtaining serum levels in human patients corresponding to at least 1, 5, 10, 25, 50, 75, or 100 µg/ml.

Exemplary doses include milligram or microgram amounts of the compound per kilogram of subject or sample weight (e.g., about 1 milligram per kilogram to about 200 milligrams per kilogram, about 5 milligram per kilogram to about 100 milligram per kilogram, about 10 milligram per kilogram to about 50 milligrams per kilogram). Additional exemplary doses include doses of about 1 to about 500 mg, or about 5 to about 300 mg, or about 10 to about 200 mg daily, twice or trice daily, or lower or higher amounts. For comparison, exemplary doses for Eprodisate (1,3-propanedisulfonic acid sodium salt) for the treatment of AA amyloidosis is about 400 mg, 800 mg or 1200 mg BID (two times per day) base on the patient's creatine clearance. See also published US patent application No. US 2006/0252829, which is incorporated herein by reference.

It is generally advantageous to formulate parenteral compositions in dosage unit form for ease of administration and uniformity of dosage. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical vehicle. In an embodiment, the compositions according to the invention are formulated in a unit dosage form, each dosage containing from about 100 mg to about 2000 mg, more preferably about 200 mg to about 1000 mg, even more preferably about 400 mg to about 800 mg of the compound according to the invention. See also published US patent application No. US 2006/0252829, which is incorporated herein by reference. The specification for the dosage unit forms of the invention may vary and are dictated by and directly dependent on (a) the unique characteristics of the therapeutic agent and the particular therapeutic effect to be achieved, and (b) the limitations inherent in the art of compounding such a therapeutic agent for the treatment of amyloid deposition in subjects.

Administration of the compounds and compositions of the present invention to a subject to be treated can be carried out using known procedures, at dosages and for periods of time effective to achieved a desired purposes (e.g. prevention or treatment of nephropathy, improvement of kidney function in general, and/or prevention and/or treatment of a blood lipids-associated condition, etc). Dosage regimens can be adjusted to provide the optimum therapeutic response. For example, several divided doses may be administered daily or the dose may be proportionally reduced as indicated by the exigencies of the therapeutic situation.

In one embodiment, the compound(s) of the invention is administered at a therapeutically effective dosage sufficient to positively affect, impact and/or modify a kidney function parameter such as albuminuria, proteinuria, creatinine clearance, urea clearance. In another embodiment, the compound(s) of the invention is administered at a therapeutically effective dosage sufficient to positively affect, impact and/or modify circulating blood levels and/or ratios of triglycerides, cholesterol, high-density lipoprotein cholesterol (HDLC), very low density lipoprotein cholesterol (VLDLC), low density lipoprotein cholesterol (LDLC), intermediate density lipoprotein cholesterol, low density lipoprotein (LDL), high density lipoprotein (HDL), and free fatty acids.

When referring to a positive effect, impact and/or modification of a kidney function parameter or circulating blood levels a "therapeutically effective" dosage refers to a modification (e.g. slowing of decline of renal function, lowering circulating harmful lipids levels) for example, of at least about 1%, or by at least about 5%, or by at least about 10%, or by at least about 20%, or by at least about 40%, or by at least about 50%, or by at least 60%, or by at least 75%, or even by at least about 100%, or more relative to untreated subjects.

Co-Administration

The method of treatment of the present invention may also include co-administration of the at least one compound according to the invention, e.g., 1,3-propanedisulfonic acid or a pharmaceutically acceptable salt thereof together with the administration of another therapeutically effective agent for the prevention or treatment of a renal disorder or complication, nephropathy (e.g. diabetic nephropathy), diabetes, dyslipidemia, hypertension and/or obesity.

In one embodiment, the compound(s) of the invention is used in combination with at least one additional known compound which is currently being used or is in development for preventing or treating diabetes. Examples of such known compounds include but are not limited to common anti-diabetic drugs such as sulphonylureas (e.g. glicazide, glipizide), mefformin, glitazones (e.g. rosiglutazone, pioglitazone), prandial glucose releasing agents (e.g. repaglinide, nateglinide) and acarbose.

In one embodiment, the compound(s) of the invention is used in combination with at least one additional known compound which is currently being used or is in development for preventing or treating renal disorder such as nephropathy, or an associated disorder or complication. Examples of such known compounds include but are not limited to: ACE inhibitor drugs (e.g. captopril (Capoten®), enalapril (Innovace®)), fosinopril (Staril®), lisinopril (Zestril®), perindopril (Coversyl®), quinapril (Accupro®), trandanalopril (Gopten®), lotensin, moexipril, ramipril); RAS blockers; angiotensin receptor blockers (ARBs) (e.g. Olmesartan, Irbesartan, Losartan, Valsartan, candesartan, eprosartan, telmisartan, etc); protein kinase C (PKC) inhibitors (e.g. ruboxistaurin); inhibitors of AGE-dependent pathways (e.g. aminoguanidine, ALT-946, pyrodoxamine (pyrododorin), OPB-9295, alagebrium); anti-inflammatory agents (e.g. clyclooxigenase-2 inhibitors, mycophenolate mophetil, mizoribine, pentoxifylline), GAGs (e.g. sulodexide (U.S. Pat. No. 5,496,807)); pyridoxamine (U.S. Pat. No. 7,030,146); endothelin antagonists (e.g. SPP 301), COX-2 inhibitors, PPAR-γ antagonists and other compounds like amifostine (used for cisplatin nephropathy), captopril (used for diabetic nephropathy), cyclophosphamide (used for idiopathic membranous nephropathy), sodium thiosulfate (used for cisplatin nephropathy), tranilast, etc. (Williams and Tuttle (2005), *Advances in Chronic Kidney Disease,* 12 (2):212-222; Giunti et al. (2006), Minerva Medica, 97:241-62).

Additionally, the methods of the invention may also include co-administration of at least one other therapeutic agent for the treatment of another disease directly or indirectly related to diabetes and/or renal disorder complications, including but not limited to: dyslipidemia, hypertension, obesity, neuropathy, and/or retinopathy, etc. Additional examples of agents that can be co-administered with the compound(s) according to the invention are corticosteroids; immunosuppressive medications; antibiotics; antihypertensive and diuretic medications (such as ACE-inhibitors); lipid lowering agents such as bile sequestrant resins, cholestyramine, colestipol, nicotinic acid, and more particularly drugs and medications used to reduce cholesterol and triglycerides (e.g. fibrates (e.g. Gemfibrozil®)) and HMG-CoA inhibitors such as Lovastatin®, Atorvastatin®, Fluvastatin®, Lescol®), Lipitor®, Mevacor®), Pravachol®, Pravastatin®, Simvastatin®, Zocor®, Cerivastatin®), etc); compounds that inhibit intestinal absorption of lipids (e.g. ezetiminde); nicotinic acid; and Vitamin D.

Therefore, an additional aspect of the invention relates to methods of concomitant therapeutic treatment of a subject, comprising administering to a subject in need thereof an effective amount of a first agent and a second agent, wherein said agent is as defined in Formula (I), and the second agent is for the prevention or treatment of renal disorders, nephropathies, diabetic nephropathy, diabetes, hypertension, hyperlipidemia or obesity.

The invention also relates to the use of at least one first agent as defined in Formula (I), and at least one second agent selected from compounds for the prevention or treatment of renal disorders, nephropathies, diabetic nephropathy, diabetes, hypertension, hyperlipidemia or obesity, for the manufacture of a medicament or kit of medicaments for the concomitant therapeutic treatment or prophylaxis of renal disorders, nephropathies, diabetic nephropathy, diabetes, hypertension, hyperlipidemia or obesity.

As used herein, the term "concomitant" as in the phrase "concomitant therapeutic treatment" includes administering a first agent in the present of a second agent. A concomitant therapeutic treatment method includes methods in which the first, second, third or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and as a second actor may administer to the subject a second agent and the administering steps may be executed at the same time, or nearly the same time, or at distant times, so long as the first agent (and/or additional agents) are after administration in the presence of the second agent (and/or additional agents). The actor and the subject may be the same entity (e.g. a human). Preferably the first agent is 3-propanedisulfonic acid or a pharmaceutically acceptable salt thereof, e.g. a disodium salt. The second agent may be selected from the list of compounds given hereinbefore.

Accordingly, the invention also provides a method for preventing, reducing or eliminating a symptom or complication of any one of the above mentioned disease or condition (e.g. diabetes, nephropathy or complication directly or indirectly related to diabetes). The method comprises administering, to a subject in need thereof, a first pharmaceutical composition comprising at least one compound of the invention and a second pharmaceutical composition comprising one or more additional active ingredients, wherein all active ingredients are administered in an amount sufficient to inhibit, reduce, or eliminate one or more symptoms or complications of the disease or condition to be treated. In one aspect, the administration of the first and second pharmaceutical composition is temporally spaced apart by at least about two minutes.

Kits

The compound(s) of the invention may be packaged as part of a kit, optionally including a container (e.g. packaging, a box, a vial, etc). The kit may be commercially used according to the methods described herein and may include instructions for use in a method of the invention. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The compound(s) of the invention may or may not be administered to a patient at the same time or by the same route of administration. Therefore, the methods of the invention encompass kits which, when used by the medical practitioner, can simplify the administration of appropriate amounts of two or more active ingredients to a patient.

A typical kit of the invention comprises a unit dosage form of a at least one compound according to the invention, e.g., 1,3-propanedisulfonic acid or a pharmaceutically acceptable salt thereof, and a unit dosage form of at least one additional active ingredient. Examples of additional active ingredients that may be used in conjunction with the compounds according to the invention, include, but are not limited to any of the compounds that could be used in combination with the compound(s) of the invention listed herein before in the section "Co-administration".

Kits of the invention can further comprise devices that are used to administer the active ingredients. Examples of such devices include, but are not limited to, syringes, drip bags, patches, inhalers, enemas, and dispensers for the administration of suppository formulations.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Assessment of Renal Function and Lipids Profiles

In order to evaluate, assess, and/or confirm the efficacy of the method, compounds and/or compositions of the invention, serial measurements of renal function of the subject can be determined.

Quantitative assessment of renal function and parameters of renal dysfunction are well known in the art and can be found, for example, in Levey (Am J Kidney Dis. 1993, 22(1): 207-214). Examples of assays for the determination of renal function/dysfunction are: serum creatinine level; creatinine clearance rate; cystatin C clearance rate, 24-hour urinary creatinine clearance, 24-hour urinary protein secretion; Glomerular filtration rate (GFR); urinary albumin creatinine ratio (ACR); albumin excretion rate (AER); and renal biopsy.

The compounds of the invention may be tested for activity in animal models. Examples of animals models of type II diabetes and obesity include: the Ob/Ob mouse (monogenic model of obesity, leptin deficient), the db/db mouse (monogenic model of obesity, leptin resistant), the Zucker (fa/fa) rat (monogenic model of obesity, leptin resistant), the Goto-Kakizaki rat, the KK mouse, the NSY mouse, the OLETF rat, the Israeli sand rat, the Fat-fed streptozotocin-treated rat, the CBA/Ca mouse, the Diabetic Torri rat, the New Zealand obese mouse (see Rees and Alcolado (2005), Diabet. Med. 22, 359-370).

Known animal models of spontaneous type 2 diabetic nephropathy include: the spontaneously hypertensive/NIH-corpulent (SHR/N-cp) rat (model of obesity, type 2 diabetes and nephropathy), the lean SHR/N-cp rat and the Wistar-Kyoto/NIH-corpulent (WKY/N-cp) rat (both allow assessment of the role of hypertension and obesity in the pathogenesis of diabetic nephropathy: the SHR/N-cp rats have abnormal glucose tolerance, hypertension, and develop a renal disease reminiscent of human diabetic nephropathy, whereas the WKY/N-cp rats are also obese and have hyperlipidaemia, but their glucose control is somewhat worse than that of the SHR/N-cp rat), and the LA/N-cp rat (also carries the gene for obesity, and exhibits hyperlipidaemia) (see Kimmel et al. (1992), *Acta Diabetologica*, Volume 29 (3-4), 142-148.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, issued patents, and published patent applications cited throughout this application are hereby incorporated by reference. The invention is further illustrated by the following examples, which should not be construed as further limiting.

EXAMPLES

The Examples set forth herein below provide exemplary formulations of certain representative compounds of the invention. Also provided are exemplary methods for assaying the compounds of the invention for renal damage and related complications.

Unless otherwise indicated, all numbers expressing quantities of ingredients, reaction conditions, concentrations, properties, and so forth used in the specification and claims are to be understood as being modified in all instances by the term "about." At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

Example 1

An example of a formulation of a 400 mg capsule of 1,3 propanedisulfonic acid disodium salt is described below.

Capsules of 400 mg of 1,3 propanedisulfonic acid disodium salt were manufactured by filling #0 white opaque hard gelatin capsules with a white powder comprised of 400 mg of 1,3 propanedisulfonic acid disodium salt and 40 mg of excipients.

| Raw Material | Grade | Function | Label (mg/unit) | % |
|---|---|---|---|---|
| 1,3 Propanedisulfonic Acid Disodium Salt (PDS) | MHS * | active | 400.0 | 90.9 |

-continued

| Raw Material | Grade | Function | Label (mg/unit) | % |
|---|---|---|---|---|
| Lactose Monohydrate (316 Fast-Flo) | NF | diluent | 37.8 | 8.6 |
| Magnesium Stearate | NF | lubricant | 2.2 | 0.5 |
| Sub-Total | | | 440.0 | 100.0 |
| # 0 Hard Gelatin Capsule | MHS * | capsule | 96.0 | |
| Total | | | 536.0 | |

* MHS—Manufacturer House Standard

Example 2

A pharmaceutical composition is formulated as described in Example 1 with 1,3 propanedisulfonic acid as the active agent.

Example 3

A pharmaceutical composition is formulated as described in Example 1 with 1,2-ethanedisulfonic acid as the active agent.

Example 4

A pharmaceutical composition is formulated as described in Example 1 with sodium 1,2-ethanedisulfonate as the active agent.

Example 5

A pharmaceutical composition is formulated as described in Example 1 with 1,2-ethanediol bis(hydrogen sulfate) as the active agent.

Example 6

A pharmaceutical composition is formulated as described in Example 1 with 1,2-ethanediol disulfate disodium salt as the active agent.

Example 7

A pharmaceutical composition is formulated as described in Example 1 with 1,3-propanediol bis(hydrogen sulfate) as the active agent.

Example 8

A pharmaceutical composition is formulated as described in Example 1 with 1,3-propanediol disulfate disodium salt as the active agent.

Example 9

A pharmaceutical composition is formulated as described in Example 1 with 2-sulfomethyl-1,4-butanedisulfonic acid as the active agent.

Example 10

A pharmaceutical composition is formulated as described in Example 1 with 2-sulfomethylbutane-1,4-disulfonic acid trisodium salt as the active agent.

Example 11

In vivo Preventive Study of Renal Function

The compound 1,3 Propanedisulfonic Acid Disodium Salt (PDS) was selected for a preventive study of renal function in the Zucker rat (ZDF) mode.

Background

Diabetic nephropathy (DN) is the most common cause of chronic kidney failure and end-stage renal disease. Increasing evidence suggests that dyslipidemia, a condition ubiquitously observed in diabetes, is a major independent contributing factor to the progression of DN.

A leading study model for DN is the inbred Zucker Diabetic Fatty rat (ZDF). Given a diabetogenic diet, the ZDF rat will closely mimic human adult onset diabetes (Type 2) and related complications including glomerulosclerosis and renal damage earlier than when fed a normal diet (i.e. 14-18 weeks of age). In addition, obesity, mild hypertension, hypertriglyceridemia, hypercholesterolemia, fasting hyperglycemia, impaired glucose tolerance and hyperinsulinemia, are all major phenotypes featured in the ZDF rat.

Aim

This pre-clinical investigation evaluates the role and efficacy of 1,3 Propanedisulfonic Acid Disodium Salt (PDS) (Eprodisate Disodium) as a preventive treatment for DN and related pathophysiology in the ZDF rat model. The primary measured outcome is the attenuation/reversal of creatinine clearance deterioration and of proteinuria. The secondary measured outcome is the impact on the metabolic status in this model.

Methods

Thirty-two, 6 week-old male ZDF rats (Charles River, St. Constant, Canada) were randomized in 2 groups, Treated (PDS; in 1% sucrose drinking solution) and Control (1% sucrose drinking solution), and studied for a period of 8 weeks. PDS was initially given in high dose (avg: 4270 mg/kg/day) during week 1, followed by an intermediate low dose (avg: 592 mg/kg/day) during weeks 2-5, and finally slightly increased during weeks 6-8 (FIG. 1). All rats were fed a high sucrose/high fat diabetogenic diet (Harlan™ TD95217). Body weight, food and drinking solution consumption were measured on a daily basis. Twelve rats from each group were individually housed in metabolic cages for a period of 24 hours once a week. During week 2, 3, 4 and 5, rats placed in metabolic cages received drinking solution but were placed in fasting condition, whereas during weeks 1, 3, 6, 7, and 8, rats were given ad libitum access to food and drinking solution. At the end of each metabolic cage session, urine output was measured, and blood and urine samples were collected in order to quantify serum and/or urine levels of PDS, creatinine, protein, uric acid, triglycerides, glucose, and electrolytes. These variables were used to calculate creatinine clearance ($C_{Cr}$) and proteinuria, and to evaluate general metabolic and renal health status.

Results

The results are presented in FIGS. 1 to 4. Results for each time point are represented as mean±SE. Trend statistics are calculated by repeated measures ANOVA, with $p<0.02$ considered statistically significant.

Treated animals were given daily an increased amount of PDS as the study progressed (FIG. 1).

Figure 3A:
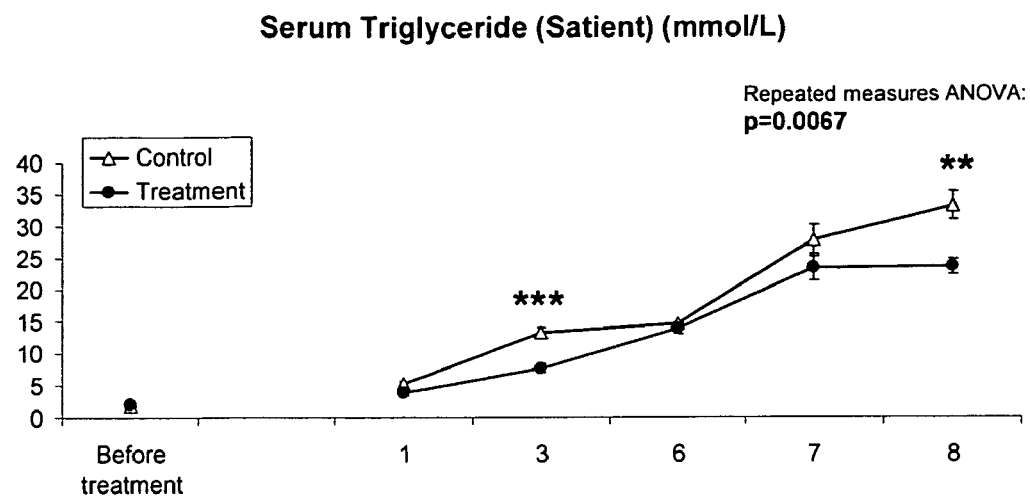
FIG. 3A is a line graph showing measured serum triglycerides in control and treated satient Zucker diabetic obese male rats, over a period of 8 weeks, according to Example 11.
Figure 3B:
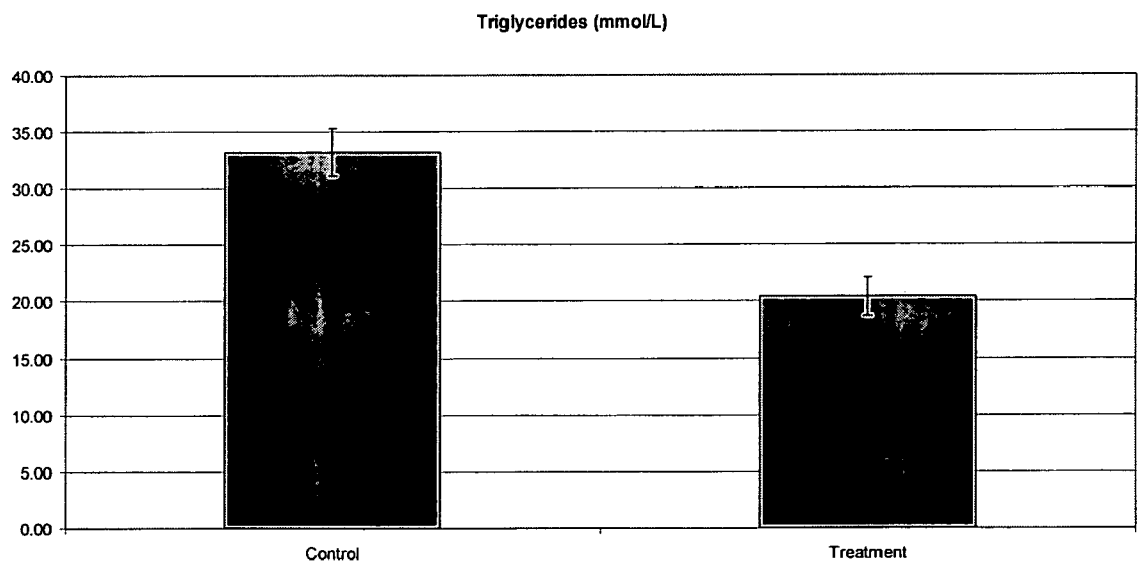
FIG. 3B is a bar graph showing measured serum triglycerides for control and treated satient Zucker diabetic obese male rats at week 8.
Figure 4A:
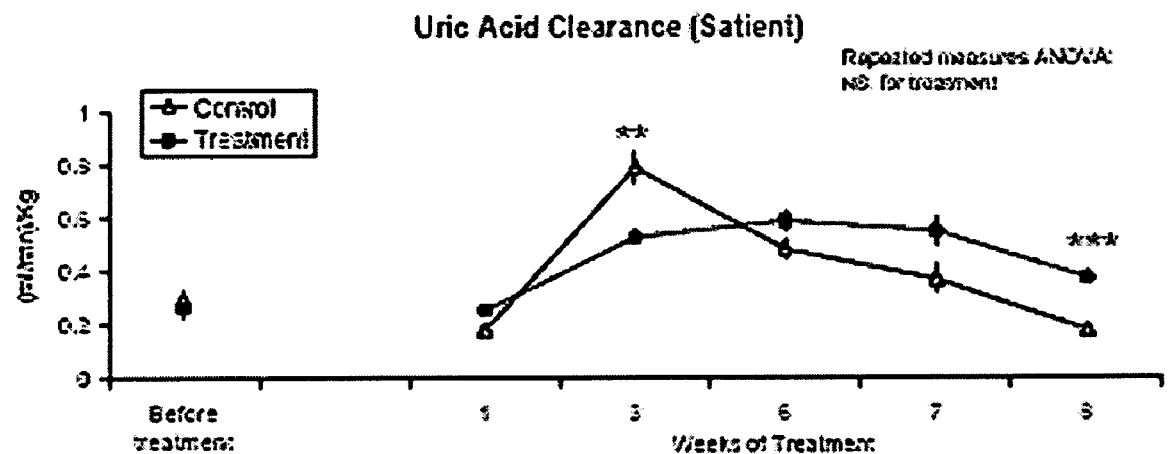
FIG. 4A is a line graph showing uric acid clearance in control and treated satient Zucker diabetic obese male rats, over a period of 8 weeks, according to Example 11.
Figure 4B:
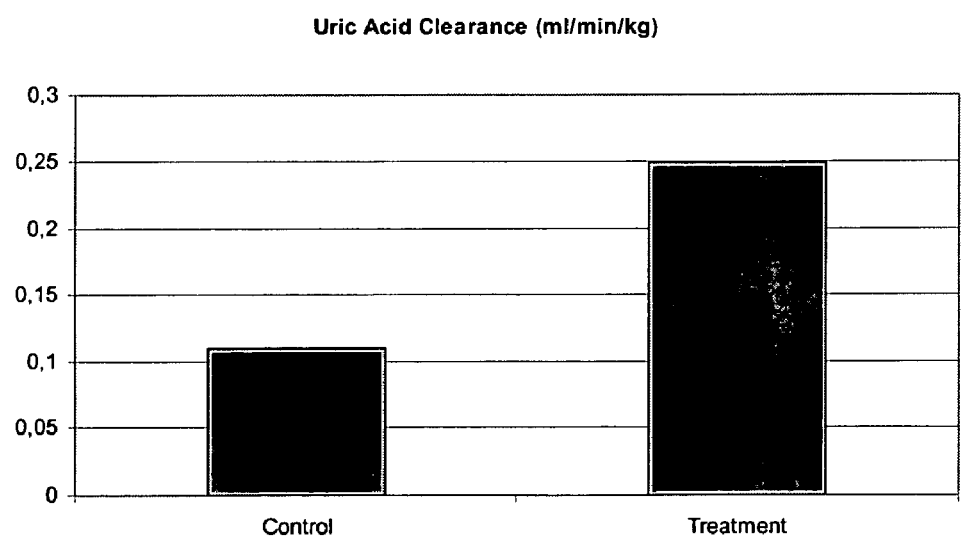
FIG. 4B is a bar graph showing uric acid clearance in control and treated satient Zucker diabetic obese male rats at week 8.

As expected, the bodyweight of the animals increased over the study (with a little decline at the beginning of the study due to diarrhea) from about 175 g to about 500 g after 60 days. There was not significant difference in the bodyweight of the treated vs. the control animals (data not shown). However, the overall health of the animals should be increasingly compromised as diabetic nephropathy develops over the test period. The study found that PDS is well tolerated at adjusted higher dose in satient condition. For results obtained in satient condition, after 8 weeks of treatment, PDS significantly lowered the degree of decline of $C_{Cr}$ normalized over body weight ($C_{Cr}$/BW) versus Control animals (p=0.012) (FIGS. 2A and 2B) and reduced serum triglyceride levels versus Control animals (p=0.0067) (FIGS. 3A and 3B). There was also a trend in the positive effect of treatment with PDS for uric acid clearance with a significant difference compared to the control group at week 8 (FIGS. 4A and 4B).

Although not shown, a preliminary evaluation of kidney mass of rats sacrificed at about 9 weeks of treatment showed that treated rats appeared to have a greater kidney mass than control rats, suggesting that treatment with PDS may also be beneficial for preserving the integrity and mass of the kidneys as compared to the control. A preliminary evaluation of the mass of the hearth ventricles showed that treated rats appeared to have a slightly lower ventricular mass, suggesting that treatment with PDS may be beneficial for preserving heart integrity and decreasing ventricular hypertrophy, hyperplasia and/or cardiomyopathy in general. These phenomena could be related to a lessening of hypertension, although this was not measured in the study. No amyloid deposit was detected in the kidneys of either group. Taken together, those results suggests that 1,3 Propanedisulfonic Acid Disodium Salt (PDS) protects renal function evidenced by the preservation of $C_{Cr}$/BW, by the reduction of uric acid serum levels, and by the reduction of serum triglycerides which may independently contribute to the prevention of renal dysfunction.

Example 12

Treatment of Human Patients

A patient requiring treatment for diabetic neuropathy is treated with 1,3 Propanedisulfonic Acid Disodium Salt (PDS) (800 mg) twice daily. The dose is adjusted by the physician (e.g. increased to 1200 mg or lowered to 400 mg) according to the patient's response to the treatment as measured by its renal function (e.g. GFR, creatinine clearance, uric acid clearance, albuminuria, etc.).

The invention claimed is:

1. A method for treating diabetic nephropathy in a subject in need thereof, comprising administering to said subject a therapeutically effective amount of 1,3-propanedisulfonic acid or a pharmaceutically acceptable salt thereof.

2. The method of claim 1, wherein said compound is 1,3-propanedisulfonic acid sodium salt.

3. The method of claim 1, wherein clearance of creatinine and/or clearance of uric acid is improved in the subject subsequent to said administration.

4. The method of claim 2, wherein said compound is 1,3-propanedisulfonic acid disodium salt.

5. The method of claim 2, wherein clearance of creatinine and/or clearance of uric acid is improved in said subject subsequent to said administration.

6. The method of claim 2, wherein said subject does not have amyloidosis.

7. The method of claim 6, wherein said subject does not have AA-amyloidosis.

8. The method of claim 3, wherein said compound is 1,3-propanedisulfonic acid sodium salt.

9. The method of claim 8, wherein said compound is 1,3-propanedisulfonic acid disodium salt.

10. The method of claim 3, wherein said subject does not have amyloidosis.

11. The method of claim 10, wherein said subject does not have AA-amyloidosis.

12. The method of claim 1, wherein said wherein said subject does not have amyloidosis.

13. The method of claim 12, wherein said subject does not have AA-amyloidosis.

14. The method of claim 12, wherein said compound is 1,3-propanedisulfonic acid sodium salt.

15. The method of claim 14, wherein said compound is 1,3-propanedisulfonic acid disodium salt.

16. The method of claim 12, wherein clearance of creatinine and/or clearance of uric acid is improved in said subject subsequent to said administration.

17. The method of claim 1, wherein said subject does not have AA-amyloidosis.

18. The method of claim 17, wherein clearance of creatinine and/or clearance of uric acid is improved in said subject subsequent to said administration.

19. The method of claim 17, wherein said compound is 1,3-propanedisulfonic acid sodium salt.

20. The method of claim 19, wherein said compound is 1,3-propanedisulfonic acid disodium salt.

21. The method of claim 1, wherein said compound is 1,3-propanedisulfonic acid disodium salt.

22. The method of claim 21, wherein clearance of creatinine and/or clearance of uric acid is improved in said subject subsequent to said administration.

23. The method of claim 21, wherein said subject does not have amyloidosis.

24. The method of claim 23, wherein said subject does not have AA-amyloidosis.

25. The method of claim 1, wherein said therapeutically effective amount is 400 mg, 800 mg or 1,200 mg BID.

* * * * *